United States Patent
Multhoff

(10) Patent No.: US 12,053,505 B2
(45) Date of Patent: Aug. 6, 2024

(54) Hsp70 BASED COMBINATION THERAPY

(71) Applicant: MULTIMMUNE GMBH, Munich (DE)

(72) Inventor: Gabriele Multhoff, Munich (DE)

(73) Assignee: MULTIMMUNE GMBH, Munich (DE)

( * ) Notice: Subject to any disclaimer, the term of this patent is extended or adjusted under 35 U.S.C. 154(b) by 0 days.

(21) Appl. No.: 16/636,741

(22) PCT Filed: Aug. 31, 2018

(86) PCT No.: PCT/EP2018/073496
§ 371 (c)(1),
(2) Date: Feb. 5, 2020

(87) PCT Pub. No.: WO2019/043170
PCT Pub. Date: Mar. 7, 2019

(65) Prior Publication Data
US 2020/0237860 A1    Jul. 30, 2020

(30) Foreign Application Priority Data

Aug. 31, 2017 (EP) ............................ 17188848

(51) Int. Cl.
| | |
|---|---|
| A61K 38/17 | (2006.01) |
| A61K 9/00 | (2006.01) |
| A61K 35/17 | (2015.01) |
| A61K 38/48 | (2006.01) |
| A61K 39/395 | (2006.01) |
| A61P 35/00 | (2006.01) |

(52) U.S. Cl.
CPC ........ *A61K 38/1709* (2013.01); *A61K 9/0019* (2013.01); *A61K 35/17* (2013.01); *A61K 38/482* (2013.01); *A61K 39/3955* (2013.01); *A61K 39/39558* (2013.01); *A61P 35/00* (2018.01); *C12Y 304/21079* (2013.01)

(58) Field of Classification Search
CPC .. A61K 38/1709; A61K 35/17; A61K 9/0019; A61K 39/3955
See application file for complete search history.

(56) References Cited

U.S. PATENT DOCUMENTS

| | | | |
|---|---|---|---|
| 7,396,681 B1 * | 7/2008 | Multhoff ............ | A61K 38/2013 435/372 |
| 7,745,399 B2 * | 6/2010 | Multhoff ............ | C12N 5/0646 514/19.3 |
| 2006/0111285 A1 | 5/2006 | Multhoff | |
| 2010/0034772 A1 | 2/2010 | Dressel et al. | |

FOREIGN PATENT DOCUMENTS

| | | |
|---|---|---|
| WO | 2005/054295 A2 | 6/2005 |
| WO | 2016/040892 A1 | 3/2016 |

OTHER PUBLICATIONS

Bowie et al., Deciphering the Message in Protein Sequences: Tolerance to Amino Acid Substitutions, Science, 1990, 247:1306-1310 (Year: 1990).*
Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Biol. 111:2129-2138, 1990 (Year: 1990).*
Lazar et al., Transforming Growth Factor ox: Mutation of Aspartic Acid 47 and Leucine 48 Results in Different Biological Activities, Mol. Cell. Biol., 8:1247-1252, 1988 (Year: 1988).*
Shevtsov et al., Heat Shock Protein-Peptide and HSP-Based immunotherapies for the Treatment of Cancer, Front. Immunol. 7:171, Publication Date: Apr. 29, 2016 (Year: 2016).*
Opdivo, Reference ID: 4012385 (Year: 2016).*
Thibult et al., PD-1 is a novel regulator of human B-cell activation, International Immunology, 25, No. 2, pp. 129-137, Publication Date: Oct. 18, 2012 (Year: 2012).*
Hildebrandt et al., Pharmacogenomics of platinum-based chemotherapy in NSCLC, Expert Opin. Drug Metab. Toxicol. (2009) 5(7): 745-755, Publication Date: May 15, 2009 (Year: 2009).*
Wangpaichitr et al., Relationship of Metabolic Alterations and PD-L1 Expression in Cisplatin Resistant Lung Cancer, Cell Dev. Biol. 6:2, Publication Date: Apr. 28, 2017 (Year: 2017).*
Belka et al., Impact of localized radiotherapy on blood immune cells counts and function in humans, Radiotherapy and Oncology, 50 (1999) 199-204, Publication year: 1999 (Year: 1999).*
Grossenbacher et al., Leveraging natural killer cells for cancer immunotherapy, Immunotherapy, 2017 9(6), 487-497, Publication Date: May 5, 2017 (Year: 2017).*
Pfister et al., Patient Survival by Hsp70 Membrane Phenotype, Cancer vol. 10, No. 4, 926-935, Publication Date: Jun. 19, 2007 (Year: 2007).*
Multimmune GmbH, "mi-Therapeutics Pipeline", 2020, https://www.multimmune.com/mi-THERAPEUTICS-PIPELINE, 6 pages.
Brown et al., "Evidence for an association between heat shock protein 70 and the respiratory syncytial virus polymerase complex within lipid-raft membranes during virus infection", Virology, 2005, vol. 338, pp. 69-80.

(Continued)

*Primary Examiner* — Peter J Reddig
*Assistant Examiner* — Cheng Lu
(74) *Attorney, Agent, or Firm* — MH2 TECHNOLOGY LAW GROUP, LLP

(57) ABSTRACT

Provided are combination therapies for treating and preventing relapse of a tumor and infectious diseases in a subject, as well as methods for use thereof. The combination therapies comprise an Hsp70 based pharmaceutical ingredient and at least one further immunotherapeutic agent that specifically inhibits and/or preferably binds to an immune checkpoint molecule or tumor immune microenvironment immune regulator. Furthermore, a kit and methods of using the combination therapies of the invention are described.

18 Claims, 6 Drawing Sheets

Specification includes a Sequence Listing.

(56) References Cited

OTHER PUBLICATIONS

Santoro et al., "Role of Heat Shock Proteins in Viral Infection", Prokaryotic and Eukaryotic Heat Shock Proteins in Infectious Disease, Oct. 2009, vol. 4, pp. 51-84.
Wykes et al., "Immune checkpoint blockade in infectious diseases", Nat Rev Immunol., Feb. 2018 February, vol. 18, No. 2, pp. 91-104.
International Search Report dated Nov. 23, 2018 from International Application No. PCT/EP2018/073496 (Authorized officer, Eva Bohmerova), 13 pages.
Brahmer et al., "Nivolumab versus Docetaxel in Advanced Squamous-Cell Non-Small-Cell Lung Cancer", New England Journal of Medicine, Jul. 9, 2015, vol. 373, No. 2, pp. 123-135.
Rao et al., "Anti-PD-1/PD-LI therapy for infectious diseases: learning from the cancer paradigm", International Journal of Infectious Diseases, vol. 56, Mar. 2017, pp. 221-228.

\* cited by examiner

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Epitope recognized by anti-Hsp70 antibody
      (cmHsp70 antibody)

<400> SEQUENCE: 1

Asn Leu Leu Gly Arg Phe Glu Leu
1               5

<210> SEQ ID NO 2
<211> LENGTH: 14
<212> TYPE: PRT
<213> ORGANISM: Artificial Sequence
<220> FEATURE:
<223> OTHER INFORMATION: Epitope recognized by anti-Hsp70 antibody
      (cmHsp70 antibody)

<400> SEQUENCE: 2

Thr Lys Asp Asn Asn Leu Leu Gly Arg Phe Glu Leu Ser Gly
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Hsp70 derived peptide
<220> FEATURE:
<221> NAME/KEY: PEPTIDE
<222> LOCATION: (1)..(14)
<223> OTHER INFORMATION: Peptide derived from Hsp70, wherein X is T or S

<400> SEQUENCE: 3

Thr Lys Asp Asn Asn Leu Leu Gly Arg Phe Glu Leu Xaa Gly
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Hsp70 derived peptide
<220> FEATURE:
<221> NAME/KEY: PEPTIDE
<222> LOCATION: (1)..(4)
<223> OTHER INFORMATION: Peptide fragment derived from Hsp70

<400> SEQUENCE: 4

Thr Lys Asp Asn
1
```

```
<210> SEQ ID NO 5
<211> LENGTH: 13
<212> TYPE: PRT
<213> ORGANISM: Artificial Sequence
<220> FEATURE:
<223> OTHER INFORMATION: human-derived TKD peptide

<400> SEQUENCE: 5

Thr Lys Asp Asn Asn Leu Leu Gly Arg Phe Glu Leu Ser
1               5                   10

<210> SEQ ID NO 6
<211> LENGTH: 14
<212> TYPE: PRT
<213> ORGANISM: Artificial Sequence
<220> FEATURE:
<223> OTHER INFORMATION: human TKD sequence peptide

<400> SEQUENCE: 6

Thr Lys Asp Asn Asn Leu Leu Gly Arg Phe Glu Leu Ser Gly
1               5                   10

<210> SEQ ID NO 7
<211> LENGTH: 14
<212> TYPE: PRT
<213> ORGANISM: Artificial Sequence
<220> FEATURE:
<223> OTHER INFORMATION: mouse TKD sequence peptide

<400> SEQUENCE: 7

Thr Arg Asp Asn Asn Leu Leu Gly Arg Phe Glu Leu Ser Gly
1               5                   10
```

Hsp70 BASED COMBINATION THERAPY

CROSS-REFERENCE TO RELATED APPLICATIONS

This application is a U.S. National Stage application of PCT/EP2018/073496 filed 31 Aug. 2018, which claims priority to European Application No. 17188848.0 filed 31 Aug. 2017, the entire disclosures of which are hereby incorporated by reference in their entireties.

SEQUENCE LISTING

The present application contains a Sequence Listing which has been submitted electronically in ASCII format and is hereby incorporated by reference in its entirety. Said ASCH copy, created on 21 Jan. 2020, is named sequence listing.txt and is 2 Kilobytes in size.

FIELD OF THE INVENTION

The present invention relates to combination therapies for treating and preventing relapse of a tumor and infectious diseases in a subject, as well as methods for use thereof. The combination therapies comprise (a) an Hsp70 based pharmaceutical ingredient such as ENKASTIM™, an Hsp70-based peptide capable of activating NK cells with targeting and killing ability towards membrane Hsp70-positive tumors and metastases and NK cells activated ex vivo with said peptide, respectively, and (b) at least one further immunotherapeutic agent, other than the Hsp70 based ingredient, that specifically inhibits and preferably binds to an immune checkpoint molecule such as PD1 or (to) a tumor immune microenvironment immune regulator such as indoleamine 2,3-dioxygenase (IDO1). The present invention also relates to a kit and methods of using the combination therapies of the invention.

BACKGROUND TO THE INVENTION

Cancer is a leading cause of premature deaths in the developed world, and infectious diseases are one of the main causes of premature deaths in the Third World and advanced developing countries. The aim of immunotherapy in cancer and infectious diseases is to mount an effective immune response by the body against the diseased cell, i.e. tumor cell and infected cell. This may be achieved by, for example, breaking tolerance against tumor antigen, augmenting anti-tumor immune responses, and stimulating local immunological responses at the tumor site or site of the infection.

Although progress in the development of new cancer therapies for the majority of tumor entities progresses at a pace, key challenges in the management and treatment of aggressive disease remain. Another big challenge relates to the time and cost of drug development, and thereby the ability of the healthcare providers to afford the therapeutics that are developed. The identification of more "universal" targeting structures that are present across different cancer entities will consolidate the costs of developing therapies during the pre-clinical and early clinical phases.

Thus, the technical problem underlying the present invention was to provide means and methods for a specific treatment of diseases and in particular of tumors, viral and bacterial infections, and inflammatory diseases.

The solution to the technical problem is achieved by providing the embodiments characterized in the claims.

SUMMARY OF THE INVENTION

The present invention is based on the surprising observations in a clinical trial after treatment of a tumor patient suffering from non-small cell lung carcinoma (NSCLC) with radiochemotherapy (RCT) that the level of B cells, which substantially dropped during the RCT treatment could be recovered and reached normal levels after natural killer (NK) cell therapy with NK cells that had been stimulated ex vivo with Hsp70 peptide ENKASTIM™ (synthetic peptide that mimics Hsp70) and further increased after the NK cell treatment and remained substantially unaffected in kind after subsequent therapy with anti-PD-1/PD-L1 pathway blockade with anti-PD-1 antibody Nivolumab, an inhibitor of the immune checkpoint molecule PD-1; see the Example and the FIG. 3A. This observation was accompanied by the fact that the patient, who otherwise would have had a median survival rate of <15 months, was still tumor-free after 18 and 32 months, respectively. Furthermore, the combination therapy was accompanied by the observation of a reduction in immunosuppressive regulatory T (Treg) cells, increased level of cytotoxic $CD8^+$ T cells and a stable maintenance of NK cells; see Example 2 and FIGS. 3B to 3F. In addition, the combined approach consisting of sequential NK cell and anti-PD-1 therapy has been shown to result in long-term tumor control which is accompanied by a massive immune cell infiltration in a preclinical glioblastoma model; see Example 3 and Tables 3 and 4.

Without intending to be bound by theory, it is believed that inter alia the drastic and fast recovery and increase in B cells might explain the beneficial outcome of the combination therapy so far. In particular, the observation of the fact that administration of an Hsp70 based ingredient, here Hsp70 peptide ex vivo stimulated NK cells, leads to a continuous increase of B cells, maintenance of NK cells and decrease of immunosuppressive regulatory T cells which is probably due to the previous Hsp70 based therapy, are not affected by the subsequent treatment with a different immunomodulator, i.e. an inhibitor of an immune checkpoint molecule such as PD-1 leads to the successful combating and prevention and relapse of the tumor. Rather than using ex vivo stimulated NK cells, also Hsp70 protein or a peptide thereof may be used for in vivo stimulation of the NK cells in the subject to be treated. Furthermore, since as shown in FIG. 7, Hsp70 serum levels are higher in a tumor patient compared to healthy individuals, other Hsp70 specific agents may be used in addition or alternatively, for example anti-Hsp70 antibodies and/or granzyme B, the effects of which are mediated by the expression of membrane Hsp70; see also FIG. 4 for Hsp70 based ingredients.

As mentioned, the anti-tumor activity of the combined therapy consisting of pre-stimulated NK cells and PD-1 inhibition could be confirmed in a preclinical orthotopic glioblastoma animal model. In particular, mice with membrane Hsp70 positive glioblastoma were sham-treated or injected with ex vivo TKD/IL-2-activated NK cells and anti-PD-1 antibody either as a single regimen or a combined sequential therapy. Tumor volume was assessed by MR scanning, and tumor-infiltrating CD8+ T and NK1.1 cells were quantified in immunohistochemical (IHC) sections. As illustrated in Example 3, adoptive transfer of ex vivo activated NK cells followed by a PD-1 blockade results in tumor growth delay (Table 3) and significantly enhanced overall survival (OS) of glioblastoma-bearing mice. Tumor control was associated with a massive infiltration of CD8+ T and NK1.1 cells; see Table 4.

In summary, a combined approach consisting of Hsp70 based treatment and blockade of immune checkpoint inhibitors illustrated by sequential NK cell and anti-PD-1 therapy is well tolerated and results in long-term tumor control which is accompanied by a massive immune cell infiltration in a preclinical glioblastoma model and a patient with advanced stage NSCLC. In view of the consistency of the preclinical and clinical data, the glioblastoma animal model provides a suitable tool for validating the combination of Hsp70 based treatment and blockade of immune checkpoint inhibitor other than specifically illustrated in the appended Examples.

Accordingly, a first aspect of the invention provides a combination therapy for use in a method of treating or preventing relapse of a tumor or an infectious disease in a subject comprising
 (a) an Hsp70 based pharmaceutical ingredient selected from the group consisting of
  (i) an Hsp70 protein which is not complexed with peptides of tumor cells, a C-terminal fragment thereof or a derivative thereof or a protein with an amino acid sequence homology to the region of amino acids 384 to 641 of the Hsp70 protein of >70%, optionally in combination with a cytokine, preferably interleukin-2 (IL-2);
  (ii) peripheral blood mononuclear cells (PBMCs) or a fraction thereof activated in vitro by said Hsp70 protein, fragment or a derivative thereof; or any combination thereof;
  (iii) an anti-Hsp70 antibody or antigen-binding fragment thereof (cmHsp70.1 antibody) that binds to an extracellular localized epitope of membrane bound Hsp70 on tumor cells or infected cells, wherein said epitope comprises or consists of the amino acid sequence NLLGRFEL (SEQ ID NO: 1) or TKDNNLLGRFELSG (SEQ ID NO: 2); and
  (iv) granzyme B, preferably recombinant granzyme B; or any combination thereof, and
 (b) at least one further immunomodulator different from (a), preferably an inhibitor of an immune checkpoint molecule such as PD-1 or tumor immune microenvironment immune regulator such as indoleamine 2,3-dioxygenase inhibitor 1 (IDO1);
 or any combination thereof.

Recently, the therapeutic strategies in the treatment of cancer utilizing autologous and allogenic NK cells, combinations of NK cells with monoclonal antibodies to induce antibody-dependent cellular cytotoxicity, or immune checkpoint inhibitors has been reviewed by the inventor in Shevtsov and Multhoff, Immunological and Translational Aspects of NK Cell-Based Antitumor Immunotherapies. Front. Immunol. 7 (2016), 492. While here a combination of ex vivo cytokine-stimulated autologous or allogenic NK cells with other immunomodulators and/or standard therapies (i.e. chemo- and radiotherapy) has been mentioned for the sake of discussion, it was concluded that further studies are necessary to elucidate the therapeutic role of the blockade of checkpoint inhibitors, which are expressed on NK cells, as well as that induced side-effects should be considered with caution.

In contrast, as mentioned above and illustrated in the Example, the patient successfully treated with the Hsp70 based combination therapy firstly received a standard radiochemotherapy (RCT), here cisplatinum-based RCT. As further explained above and shown in the Example, RCT seems to be commonly associated with a substantial decrease of B cells and NK cells which effect could be reversed by the Hsp70 based treatment. Accordingly, in a preferred embodiment, the combination therapy of the present invention either (c) comprises RCT or is applied to a subject who already received RCT or other standard care treatment that led to depletion of B lymphocytes in the subject.

A further aspect of the present invention provides a method of treating or preventing relapse of a tumor or an infectious disease in a subject comprising the subject combination therapy by administering to a subject in need thereof a therapeutically effective amount of
 (a) administering to the subject a therapeutically effect amount of the Hsp70 based pharmaceutical ingredient, preferably said peptide or activated PBMCs or fraction thereof, and currently or subsequently
 (b) administering to the subject a therapeutically effect amount of the immunomodulator;
 preferably wherein the subject had been treated prior to step (a) by radiochemotherapy and/or shows a reduced level of B cells.

In a preferred further embodiment, steps (a) and (b) are carried out simultaneously or subsequently wherein step (b) is carried out between 1 to 24 months after step (a), between 6 to 12 months after the last cycle of administration in step (a), preferably about 9 months after the last cycle of administration in step (a); and/or wherein step (a) is carried out between 1 week and 6 months after the subject had been treated by radiochemotherapy and/or received an equivalent therapy that leads to a reduced level of B cells, preferably about 1 to 4 months after the last cycle of RCT or like chemo- and/or radiotherapy.

SEQBiotechnol. 46 (2010), 206-208 and Zettlitz et al., Mol. Biotechnol. 46 (2010), 265-278.

BRIEF DESCRIPTION OF THE FIGURES

FIG. 3A: Percentage of CD19+B cells at diagnosis (V0), after RCT (V1), after CT-guided restaging (V2), after 4 cycles of NK cell therapy (V3), after 3-monthly CT-guided restaging (V4-V6), and upon 3 cycles of Nivolumab treatment (V7).

FIG. 3B: Percentage of CD3$^+$ T cells, CD4$^+$ helper T cells and CD8$^+$ cytotoxic T cells at diagnosis (V0), after RCT (V1), after CT-guided restaging (V2), after 4 cycles of NK cell therapy (V3), after 3-monthly CT-guided restaging (V4-V6), and upon 3 cycles of Nivolumab treatment (V7).

FIG. 3C: Percentage of immunosuppressive CD4$^+$/CD8$^+$ regulatory T cells at diagnosis (V0), after RCT (V1), after CT-guided restaging (V2), after 4 cycles of NK cell therapy (V3), after 3-monthly CT-guided restaging (V4-V6), and upon 3 cycles of Nivolumab treatment (V7).

FIG. 3D: Percentage of CD3$^+$/CD94$^+$/CD56$^+$ NK-like T (NKT) cells at diagnosis (V0), after RCT (V1), after CT-guided restaging (V2), after 4 cycles of NK cell therapy (V3), after 3-monthly CT-guided restaging (V4-V6), and upon 3 cycles of Nivolumab treatment (V7).

FIG. 3E: Percentage of CD3$^-$/NKG2D$^+$, CD3$^-$/NKp30$^+$, CD3$^-$/NKp46$^+$, CD3$^-$/CD56$^+$ NK cell subpopulations at diagnosis (V0), after RCT (V1), after CT-guided restaging (V2), after 4 cycles of NK cell therapy (V3), after 3-monthly CT-guided restaging (V4-V6), and upon 3 cycles of Nivolumab treatment (V7).

FIG. 3F: Percentage of CD3$^-$/CD94$^+$ NK cells at diagnosis (V0), after RCT (V1), after CT-guided restaging (V2), after 4 cycles of NK cell therapy (V3), after 3-monthly CT-guided restaging (V4-V6), and upon 3 cycles of Nivolumab treatment (V7).

Figure 1:
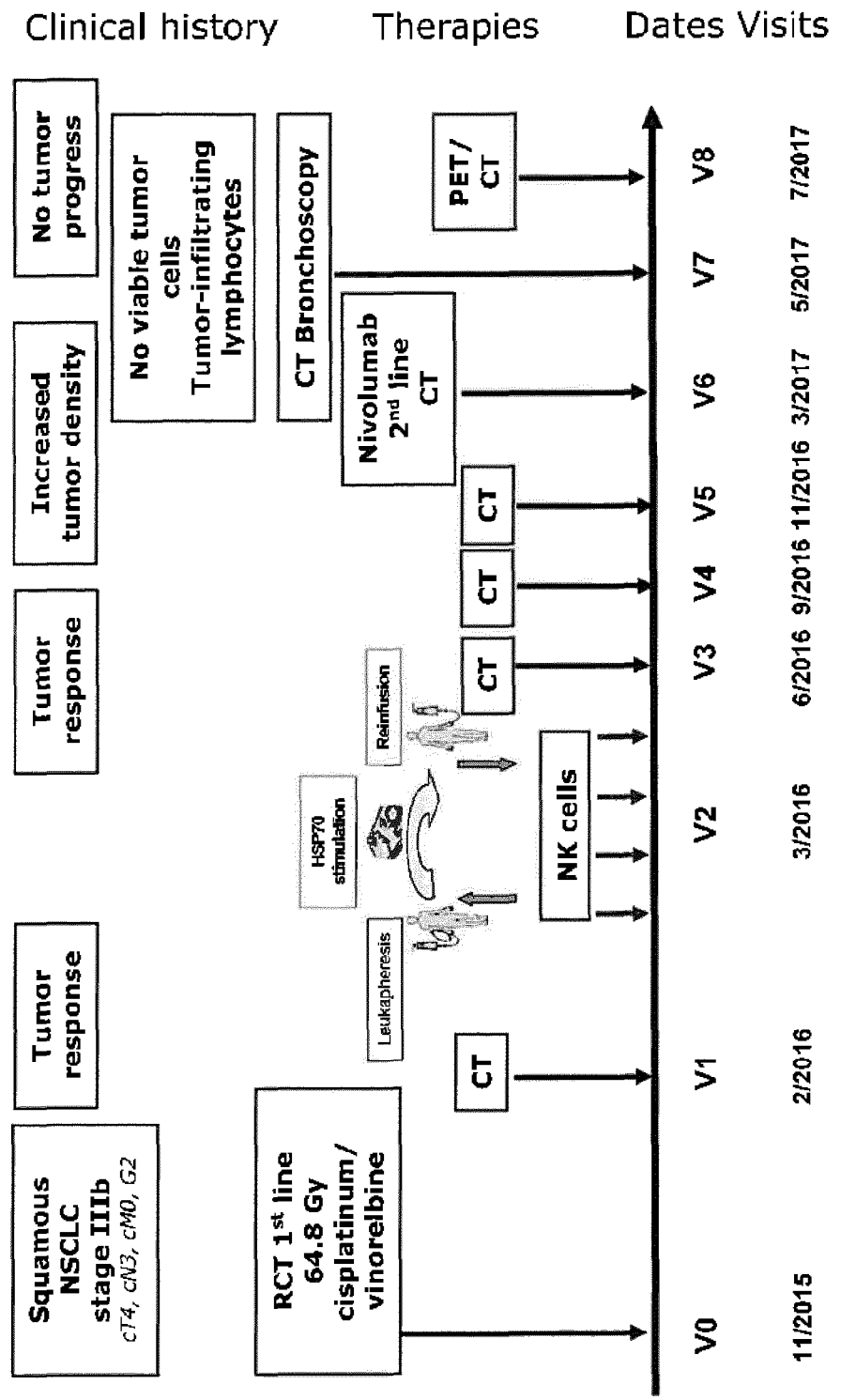
FIG. 1: Schematic representation of the clinical history, study design, visits and dates of therapy of a 58 year old male patient diagnosed with NSCLC (stage IIIB, cT4, cN3, cM0, G2) in November 2015. After simultaneous RCT a partial tumor response was determined by CT scan. 4 weeks (March 2016) later the patient received 4 cycles of ex vivo TKD/IL-2 activated, autologous NK cells on a monthly basis. After 3 sequential restagings on a three-monthly basis without any tumor progress an increased cell density was detected in the central right tumor area in February 2017. After 3 cycles of Nivolumab (March 2017 to April 2017), as a second line therapy, no tumor progress was detected. In a CT-guided bronchoscopy tumor-infiltrating lymphocytes were found. A PET-CT restaging two months later (July 2017) did not reveal any tumor progress.

ENKASTIM™-iv is an Hsp70 based GMP-grade synthetic peptide comprising 14 amino acids (14mer, TKD), which upon intravenous administration results in a specific activation of NK cells with targeting and killing ability towards membrane Hsp70-positive tumors and metastases as well as infected cells.

ENKASTIM™-ev denotes a class of therapy known as Active Cellular Immunotherapies (ACIs), wherein immune effector cells are obtained from patients by blood collection (leukapheresis) and NK cells are activated in culture (ex vivo) with Hsp70 peptide/interleukin-2 for several days in a closed system and re-delivered as an intravenous infusion. This form of Hsp70 based treatment was used in the combination therapy illustrated in the Example.

mi-TUMEXtx (cmHsp70.1 monoclonal antibody) targets surface-bound Hsp70 and has the potential to be used for the treatment of most tumor types. The administration of mi-TUMEXtx induces Antibody-Dependent Cellular Cytotoxicity (ADCC) of membrane Hsp70-positive tumors and metastases, while sparing healthy cells. mi-TUMEXtx can also be used to deliver toxic payloads to cells expressing membrane Hsp70.

mi-APO, i.e. a recombinant human form of Granzyme B, is a serine protease which targets surface-bound Hsp70 and results in a specific perforin-independent induction of apoptosis in Hsp70-positive tumors and metastases, while sparing healthy cells.

DETAILED DESCRIPTION OF THE INVENTION

It is to be understood that different applications of the disclosed combination therapies and methods may be tailored to the specific needs in the art. It is also to be understood that the terminology used herein is for the purpose of describing particular embodiments of the invention only, and is not intended to be limiting.

The terms "combination therapy" or "combined treatment" or "in combination" as used herein denotes any form of concurrent or parallel treatment with at least two distinct therapeutic agents. The term "combination therapy" also encompasses one or more pharmaceutical compositions which either contain the components of the combination therapy (a), (b) and optionally (c) or are designed to be administered according to the treatment regimen of the present invention.

By "therapeutically effective amount" of a substance, it is meant that a given substance is administered to a subject suffering from a condition, in an amount sufficient to ensure, alleviate or partially arrest the condition or one or more of its symptoms. Such therapeutic treatment may result in a decrease in severity of disease symptoms, or an increase in frequency or duration of symptom-free periods. Effective amounts for a given purpose and a given agent will depend on the severity of the disease or injury as well as the weight and general state of the subject. As used herein, the term "subject" includes any mammal, preferably a human.

A first aspect of the invention provides a combination therapy for use in a method of treating or preventing relapse of a tumor or an infectious disease in a subject comprising
(a) an Hsp70 based pharmaceutical ingredient selected from the group consisting of
  (i) an Hsp70 protein which is not complexed with peptides of tumor cells, a C-terminal fragment thereof or a derivative thereof or a protein with an amino acid sequence homology to the region of amino acids 384 to 641 of the Hsp70 protein of >70%, optionally in combination with a cytokine, preferably interleukin-2 (IL-2);
  (ii) peripheral blood mononuclear cells (PBMCs) or a fraction thereof activated in vitro by said Hsp70 protein, fragment or a derivative thereof; or any combination thereof;
  (iii) an anti-Hsp70 antibody or antigen-binding fragment thereof (cmHsp70.1 antibody) that binds to an extracellular localized epitope of membrane bound Hsp70 on tumor cells or infected cells, wherein said epitope comprises or consists of the amino acid sequence NLLGRFEL (SEQ ID NO: 1) or TKDNNLLGRFELSG (SEQ ID NO: 2); and
  (iv) granzyme B, preferably recombinant granzyme B; or any combination thereof, and
(b) at least one further immunomodulator different from (a), preferably an inhibitor of an immune checkpoint molecule or tumor immune microenvironment immune regulator;
  or any combination thereof.

As mentioned above, and illustrated in the Example, the present invention is based on a surprising therapeutic response of a carcinoma patient after a standard care treatment, here radiochemotherapy (RCT), and a subsequent Hsp70 based immunotherapy and treatment with an immune checkpoint molecule inhibitor. In particular, the present invention is based on the surprising observations that after treatment of non-small cell lung carcinoma (NSCLC) with RCT the level of B cells, which substantially dropped during the RCT treatment could be recovered and reached normal levels after natural killer (NK) cell therapy with NK cells that had been stimulated ex vivo with Hsp70 peptide ENKASTIM™ (synthetic peptide that mimics Hsp70) and further increased after the NK cell treatment and remained substantially unaffected in kind after subsequent therapy with anti-PD-1/PD-L1 pathway blockade with anti-PD-1 antibody Nivolumab, an inhibitor of the immune checkpoint molecule PD-1.

In particular, a male patient with inoperable NSCLC (cT4, cN3, cM0, stage IIIB), was treated with simultaneous cis-platinum/vinorelbine based RCT. After 4 cycles of ex vivo TKD (2 µg/ml) plus low dose IL-2 (100 IU/ml) stimulated, autologous NK cells on a monthly basis, the patient was restaged by CT-scanning every three months in the follow-up period. Ten months after start of treatment an increased tumor cell density which remained stable in size thereafter was determined in the right central tumor area by CT-imaging. Therefore, the patient received three cycles of the immune checkpoint inhibitor antibody Nivolumab, as a second line therapy. Blood samples were taken before, during and in the follow-up period for immunophenotyping by flow cytometry and for analysis of the Hsp70 serum content using the lipHsp70 ELISA.

Histological analysis of a CT-guided bronchoscopy of a patient after RCT, NK cell and Nivolumab therapy who responded to RCT showed no signs of viable tumor mass 18 months after diagnosis. Immunophenotyping of the patient's peripheral blood lymphocytes (PBL) revealed no change in the NK cell counts, a drastic increase in the percentage of B cells after NK cell therapy, higher percentages of CD8$^+$ cytotoxic T cells compared to CD4$^+$ helper T cells, and a decrease in regulatory T (Treg) cells after Nivolumab treatment. Due to the onset of inflammation, Hsp70 serum levels increased directly after NK cell and Nivolumab therapy, but decreased 2 months thereafter. As a result, a combined therapy consisting of RCT, ex vivo Hsp70 activated NK cells and checkpoint inhibitor antibody Nivolumab is well tolerated and results in a long-term tumor control which is accompanied by immune cell activation in the peripheral blood and a decrease in Hsp70 serum levels. Furthermore, neither tumor progression nor distant metastases being detectable by CT scan in the last follow-up 32 months after diagnosis.

Without intending to be bound by theory, the combination therapy and method, respectively, of the present invention is based on the presence of Hsp70 as a target structure on the surface of tumor cells only which can be recognized by NK cells that have been stimulated using a Hsp70 derived peptide, e.g. the 14-mer TKD peptide ENKASTIM™ (synthetic peptide that mimics Hsp70) in combination with an immune cell growth factor/cytokine such as IL-2. This stimulation induces the cytolytic activity of patient-derived NK cells against their own tumors. The addition of immunomodulators such as immune checkpoint inhibitors improves the killing activity of the ex vivo stimulated NK cells inside the body of the patient and thereby causes long-term protective anti-tumor immunity. While in the clinical trials ex vivo stimulated NK cells have been used, alternatively the stimulation of the NK cells may be achieved in vivo by co-administering the Hsp70 derived peptide and the cytokine. Furthermore, form some tumors, though not always necessary as a first line therapy treatment with radio- and (cisplatinum-based) chemotherapy (RCT) for tumor debulking and increasing the antigen repertoire may be applied.

The effect of a combined approach consisting of Hsp70-targeting NK cells and anti-PD-1 inhibition was also tested in a preclinical glioblastoma mouse model. A glioblastoma mouse model was used (i) because this tumor shows a high membrane Hsp70 expression comparable to NSCLC, and (ii) due to the lack of clinically relevant orthotopic NSCLC mouse models. As can be inferred from Table 3 in Example 3, over time the combined approach is far more effective than could be expected from the individual treatment with NK cells and PD-1 antibody alone, demonstrating a synergistic effect of the combination of Hsp70 based treatment with blockade of immune checkpoint inhibitor.

So far it was experienced that two active anti-tumor substances balance each other and do not lead to an additive or even long term and synergistic effect, respectively. This is particularly true for the present case.

First, despite promising results in progression-free survival of advanced tumor patients, a relevant proportion of patients does not benefit from immune checkpoint inhibitor therapies. This may be explained in part by the deficiency of antitumor specific immune cells.

Second, depending on its subcellular or extracellular localization, Hsp70 fulfils different functions. On the one hand mHsp70 serves as a tumor-specific target for Hsp70-targeting NK cells, on the other hand, high cytosolic Hsp70 levels can interfere with apoptotic pathways that mediate therapy resistance. Therefore, Hsp70-targeting as a single regimen might not be sufficient for complete tumor control.

Since there was no obvious link between immune checkpoint inhibitor therapy and Hsp70 mediated treatment of tumor cells or that these approaches could complement each other, the observation in accordance with the present invention that Hsp70 activated NK cells targeting mHsp70 positive tumors combined with immune checkpoint inhibitor therapy of a patient with mHsp70 positive, non-operable tumor exemplified with NSCLC is well tolerated, induces antitumor immune responses and results in long-term tumor control in a patient with advanced NSCLC over 1 to 3 years and that blockade of immune checkpoint inhibitor such as the PD-1 pathway after Hsp70 based activation of NK cells seems to synergistically leads to long-term control of a tumor was totally surprising.

In view of these observations it is believed that tumors expressing membrane Hsp70 (mHsp70) as a tumor-specific target are amenable to a combined attack, i.e. an Hsp70 specific anti-tumor agent such as Hsp 70 activated NK cells, the cmHsp70.1 monoclonal antibody to induce antibody-dependent cytotoxicity or human recombinant granzyme B which is specifically taken up by mHsp70 bearing tumor cells and thereby induces tumor cell killing, and a blockade of immune checkpoint inhibitors including PD-1/PD-L1 providing inhibitory feedback loops for an immune cell mediated tumor rejection in a long term fashion as observed in the clinical trial described in the Examples.

In addition, regarding the use of the anti-PD-1 antibody Nivolumab, as an inhibitor of the immune checkpoint molecule PD-1 in the Example, further pre-clinical studies undertaken in accordance with the present invention have shown that different immune checkpoint blockade reagents (e.g. anti-CTLA-4, anti-PD1, anti-PDL1; see also infra) show similar capacities to enhance the anti-tumor activity of immune cells (NK cells, T cells). Therefore, it is reasonable to assume that different immunomodulators and combinations thereof are equally effective.

Accordingly, as mentioned, in its broadest aspect the combination therapy and method, respectively, of the present invention comprises (a) administering to the subject a therapeutically effective amount of an Hsp70 based pharmaceutical ingredient, and (b) administering to the subject a therapeutically effective amount of an additional therapeutic agent, i.e. immunomodulator other than an Hsp70 based pharmaceutical ingredient. Steps (a) and (b) may be carried out simultaneously. Alternatively, and in view of the Example as a preferred embodiment steps (a) and (b) are carried our sequentially, preferably wherein step (a) precedes step (b). In step (a), the Hsp70 based pharmaceutical ingredient is preferably administered as an intravenous infusion of ex vivo activated PBMCs or NK cells, intravenous administration of TKD peptide with cytokine such as IL-2, intravenous administration of cmHsp70.1 antibody, or intravenous/intratumoral administration of granzyme B. In step (b), the immunomodulator is preferably administered intravenously over 60 min. every 2 weeks The combination therapy and method, respectively, of the present invention has several advantages. First, the Hsp70 based pharmaceutical ingredients such as Hsp70 protein derived TKD peptide ENKASTIM™ (synthetic peptide that mimics Hsp70), NK cells and granzyme B are all of human origin or can be humanized in case of an anti-Hsp70 antibody resulting in fewer side-effects than purely artificial compounds. Furthermore, the NK cell stimulation approach, either in vitro or in vivo results in an expansion of the NK cells in the human body, allowing a lower dose of the drug. Moreover, as demonstrated in the Example, application of an Hsp70 based pharmaceutical ingredient leads to recovery and increase of the level of B lymphocytes (CD3$^-$/CD19$^+$), the levels of which are severely depleted during the course of standard care tumor treatment.

Heat shock protein 70 (Hsp70) is the major stress inducible form of the heat shock protein family (HSP), which is primarily located in the cytosol. Membrane Hsp70 is most frequently expressed on a variety of different tumor types including lung, colon, breast, head and neck, stomach, pancreas carcinomas, malignant melanoma, central nervous system including glioblastoma multiforme and hematological diseases, but never on the corresponding normal tissues. In addition to primary tumors, metastases, the major cause of death by cancer, present even higher amounts of Hsp70 on their surface membranes.

Natural killer (NK) cells have been found to specifically interact with a C-terminal localized epitope of Hsp70 that is presented on the cell membrane of tumor cells. The amount of membrane-bound Hsp70 on tumor cells positively correlates with the sensitivity to the lysis mediated by NK cells: Physical (heat) as well as chemical (cytostatic drugs) stress have been found to increase Hsp70 cell surface expression on tumor cells and thereby render them better targets for NK cells. Incubation of purified NK cells with recombinant Hsp70-protein increases their cytolytic activity against Hsp70 membrane-positive tumor cells (Multhoff et. al. (1999) Exp. Hematology 27, 1627). The same effect is achieved by a 14 amino acid peptide, termed ENKASTIM™ (synthetic peptide that mimics Hsp70) and TKD (TKDNNLLGRFELSG, aa450-463), respectively, derived from the C-terminal domain of Hsp70. This region corresponds to the domain of Hsp70 exposed to the extracellular milieu of viable tumor cells. Thus, in one embodiment, the combination therapy of the present invention relies on, and is intended to bring about, the therapeutic effect via the activation of NK cells in vivo.

Surface expression of heat-shock proteins including Hsp70 has been reported to occur also after bacterial, viral, fungal or malaria infection or in response to stress. In particular, membrane Hsp70 was found on HIV-infected lymphoid cells and on HTLV I-infected rabbit cell lines. Similarly, it is conceivable that cells infected by bacteria or affected by inflammation express Hsp70 on their cell surface. Consequently, Hsp70 based pharmaceutical ingredients such as the lytic activity of NK cells or granzyme B can be directed towards tumor cells as well as cells infected by viruses or bacteria and those affected by inflammation. Furthermore, Hsp70-expressing tumor cells and infected cells can also be targeted using a monoclonal antibody which can detect the membrane form of Hsp70 (e.g. miTUMEXtx) and a serine protease (e.g. granzyme B, miAPO) which can selectively kill cancer cells and infected cells expressing the membrane form of Hsp70; see, e.g., international applications WO 1999/049881, WO 2002/022656, WO 2004/018002 and WO 2005/054295 for review, the disclosure content of which is incorporated herein by reference.

Hsp70 based anti-cancer immunotherapy including, for example, intratumorally delivered Hsp70 that penetrates cancer cells and pulls its intracellular analog outside of the cell, thereby activating cells, constituting both innate and adaptive immunity, all of which strategies are intended to be encompassed in the Hsp70 based pharmaceutical ingredient for use in the combination therapy of the present invention is reviewed by Guzhova and Margulis in Hum. Vaccin. Immunother. 12 (2016), 2529-2535, in particular Table 1 at page 2530, right column for immunomodulatory activities of Hsp70 and forms of Hsp70 vaccines and constructs, and Shevtsov and Multhoff, Immunological and Translational Aspects of NK Cell-Based Antitumor Immunotherapies. Front. Immunol. 7 (2016), 492, the disclosure content of both of which is incorporated herein by reference.

The tumor and infectious disease, respectively, to be treated, i.e. the affected cells such as tumor or tumor stromal cells express cell surface Hsp70. A membrane Hsp70-positive phenotype can be determined either directly on single cell suspensions of tumor biopsies or cell sample of infected cells by flow cytometry using cmHsp70.1 monoclonal antibody described in international application WO2005/054295, Multhoff, Mol. Biotechnol. 46 (2010), 206-208 and Zettlitz et al., Mol. Biotechnol. 46 (2010), 265-278 or indirectly in the serum of patients using a novel lipHsp70 ELISA; see international application WO 2016/120325, the disclosure content of which is incorporated herein by reference. In addition, or alternatively, the combination therapy of the present invention may further comprise administration of an agent capable of inducing the expression of Hsp70 on the cell surface of tumor cells and infected cells, for example photodynamic therapy such as photofrin-based photodynamic therapy (PDT) as described in Korbelik et al., Cancer Res. 65 (2005), 1018-1026 or chemotherapeutic inducers of apoptosis such as etoposide and camptothecin or histone deacetylase (HDAC) inhibitors; see, e.g., Jensen et al., J. Leukoc. Biol. 86 (2009), 923-932.

In a preferred embodiment of the combination therapy of the present invention, the Hsp70 derivative is a peptide comprising 30 or less amino acids, preferably wherein said peptide comprises the amino acid sequence TKDNNLLGRFELXG (SEQ ID NO: 3), wherein X is T or S, or an amino acid sequence which deviates from the amino acid sequence of SEQ ID NO: 3 by way of an amino acid substitution, wherein amino acids TKDN (SEQ ID NO: 4) and X as defined above are retained, and wherein said peptide stimulates NK cell activity. Most preferably, the peptide is ENKASTIM™ (synthetic peptide that mimics Hsp70), i.e. TKD peptide mentioned above and originally described in international application WO 2002/022656.

The use of ex vivo Hsp70-peptide-activated PBMCs, in particular autologous NK cells in the treatment of colon and lung cancer patients is described in Krause et al., Clin. Cancer Res. 10 (2004), 3699-3707. Here, after ex vivo stimulation of autologous peripheral blood lymphocytes with Hsp70-peptide TKD (2 microg/ml) plus low-dose IL-2 (100 units/ml), TKD was removed by extensive washing, and activated cells were reinfused i.v. The procedure was repeated for up to six cycles, applying a dose escalation schedule in the selected patients. Accordingly, in the combination therapy for use according to the present invention, said fraction of PBMCs comprise or substantially consist of ex vivo Hsp70-peptide TKD/IL-2 activated/expanded NK cells, preferably autologous PMBCs and NK cells, respectively. In one embodiment of the combination therapy of the present invention, the subject/patient receives 1 to 10, preferably 2 to 8, more preferably 3 to 6 and most preferably 4 cycles of infusion with NK cells, preferably autologous NK cells or corresponding treatment with an Hsp70 based ingredient that leads to NK cell activation and/or expansion in vivo.

Cell surface-bound Hsp70 mediated perforin-independent apoptosis by specific binding and uptake of granzyme B is described in Gross et al., J. Biol. Chem. 278 (2003), 41173-41181 and immunotherapeutic targeting of membrane Hsp70-expressing tumors using recombinant human granzyme B is described, for example in Gehrmann et al., PLOS One. 7 (2012), e41341.

Needless to say that the Hsp70 based pharmaceutical ingredient in the combination therapy for use in accordance with the present invention may include genetically modified proteins, peptides and cells, respectively. For example, enhanced generation of cytotoxic T lymphocytes by Hsp70 fusion proteins harboring both $CD8^+$ T cell and $CD4^+$ T cell epitopes has been described; see, e.g., Takemoto et al., Mol. Pharm. 7 (2010), 1715-1723. Likewise included in the definition of the terms used for the Hsp70 based pharmaceutical ingredient are, for example, PBMCs and PBMC fractions including T cells and NK cells that have been genetically-modified with respect to their receptors, e.g., CAR-T, CAR NK cells (for principle strategy see Shevtsov and Multhoff (2016) and Guzhova and Margulis (2016), supra) activated in vitro by said Hsp70 protein, fragment or a derivative thereof and anti-Hsp70 antibody (cmHsp70.1) drug conjugates as described in international application WO2005/054295. In one embodiment, the Hsp70 based pharmaceutical ingredient is a cmHsp70.1 monoclonal antibody-based Antibody-Drug Conjugate (ADC); see, e.g., Diamantis and Banerji, Br. J. Cancer 114 (2016), 362-367 for review.

The further component of the combination therapies of the present invention is an immunotherapeutic agent with efficacy in the treatment of cancer and infectious diseases, respectively, which agent is not an Hsp70 based ingredient. The term "immunotherapeutic agent" is intended to include any molecule, peptide, antibody or other agent which can stimulate a host immune system to generate an immune response to a tumor, cancer or infected cell in the subject. Various immunotherapeutic agents are useful in the compositions and methods described herein. In a preferred embodiment, the immunotherapeutic agent is an antibody or antigen-binding fragment thereof, or an inhibitor of molecular pathways. The term "immune response" includes T cell mediated, NK cell mediated and/or B cell mediated immune responses. Exemplary immune responses include T cell and NK cell responses, e.g., cytokine production and cellular cytotoxicity. In addition, the term immune response includes immune responses that are indirectly affected by NK and T cell activation, e.g., antibody production (humoral responses) and activation of cytokine responsive cells, e.g., macrophages.

The combination therapies of the present invention additionally comprise a further immunotherapeutic agent, effective in the treatment of cancer or an infectious disease, which preferably specifically binds to an immune checkpoint molecule and inhibits the activity of the same. It will be appreciated that the therapeutic benefit of the further immunotherapeutic agent may be mediated by attenuating the function of an inhibitory immune checkpoint molecule (i.e. an inhibitor of an immune checkpoint molecule) and/or by activating the function of a stimulatory immune checkpoint molecule (i.e. an activator of a costimulatory molecule); see also FIG. 1 in Shevtsov and Multhoff (2016), supra. Corresponding immunomodulators, in particular for use in treating cancer are known to the person skilled in the art; see, e.g., international applications WO 2016/040892 and WO 2016/023960 with further information on immune checkpoint molecules that may be targeted in accordance with the combination therapy of the present invention.

For example, an inhibitor of an immune checkpoint molecule may be chosen from an inhibitor of one or more of CD155, PD-1, PD-L1, PD-L2, CTLA4, TIM3, LAG3, VISTA, BTLA, TIGIT, LAIR1, CD160, 2B4, TGFR beta, KIRs, and CD94/NKG2A. In a particular preferred embodiment of the combination therapy of the present invention the further immunotherapeutic agent is a PD1 inhibitor, such as an anti-PD1 antibody, or antigen-binding fragment thereof capable of inhibiting PD1 function (for example, Nivolumab, Pembrolizumab, Lambrolizumab, Pidilzumab and AMP-224). Alternatively, the PD1 inhibitor may comprise or consist of an anti-PD-L1 antibody, or antigen-binding fragment thereof capable of inhibiting PD1 function (for example, MED1-4736 and MPDL3280A). The use of anti-PD1 antibody in a combination therapy for the treatment of tumors including non-small cell lung carcinoma (NSCLC) has been described; see, e.g., international applications WO 2016/023960 and WO 2016/040892 which teaching of and disclosure is intended to be applied in accordance with the present invention in that in addition, or alternatively to, at least one compound disclosed therein, an Hsp70 based ingredient is used and preferably a subject is to be treated showing a reduced level of B lymphocytes, for example due to a conventional standard care treatment such as radiochemotherapy. Likewise, regulators of the tumor immune microenvironment such as indoleamine 2,3-dioxygenase inhibitor 1 (IDO1) for use in accordance with the combination therapy of the present invention are known in the art; see, e.g., Brochez et al., European Journal of Cancer 76 (2017), 167-182; Greco et al., Future Medicinal Chemistry 8 (2015), https://doi.org/10.4155/fmc.15.165; Vacchelli et al., OncoImmunology 3 (2014), e957994-1-10; Zhai et al., Journal of Neuro-Oncology 123 (2015), 395-403; international applications WO 2004/094409 and WO2014/150677 and US patent application US 2013/0123246 A1 for review.

Optionally, the combination therapy further comprises a third immunotherapeutic agent with efficacy in the treatment of cancer or the infectious disease. For example, the combination therapies disclosed herein can also be combined with a standard cancer treatment disclosed in international application WO 2016/040892 at page 119, lines 4ff to page 137, line 15. In particular, the combination therapy disclosed herein can be further co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the combination therapy and the Hsp70 based ingredient in particular are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies. In particular, as explained above and illustrated in the Example, the combination therapy of the present invention and the use of an Hsp70 based ingredient, preferably Hsp70 peptide ENKASTIM™ (synthetic peptide that mimics Hsp70) or NK cells stimulated therewith are applied in combination with a therapeutic treatment that otherwise leads to a depletion of B cells and/or in order to maintain a high level of cytotoxic $CD3^+$ T cells and NK cells while reducing immunosuppressive regulatory T cells.

As illustrated in the Example, the tumor patient suffering from non-small cell lung carcinoma (NSCLC), stage IIIB received a simultaneous cisplatinum-based radiochemotherapy (RCT) prior to the treatment with the Hsp70 based pharmaceutical ingredient, here 4 cycles with Hsp70 peptide ENKSASTIM© ex vivo stimulated NK cells. As further explained above and shown in the Examples, RCT seems to be commonly associated with a substantial decrease of B cells and NK cells which effect could be reversed by the Hsp70 based treatment.

Accordingly, in a particular preferred embodiment, the combination therapy of the present invention further comprises or is used in combination with a standard of cancer care chemotherapeutic and radiotherapeutic agent including, but not limited to carboplatin (PARAPLATIN®), cisplatin (PLATINOL®) and others commonly used in radiochemotherapy of cancers, preferably for the treatment of non-small cell lung cancer, for example including those disclosed in international application WO 2016/040892 at page 131, line 24 to page 132, line 30.

Figure 3A:
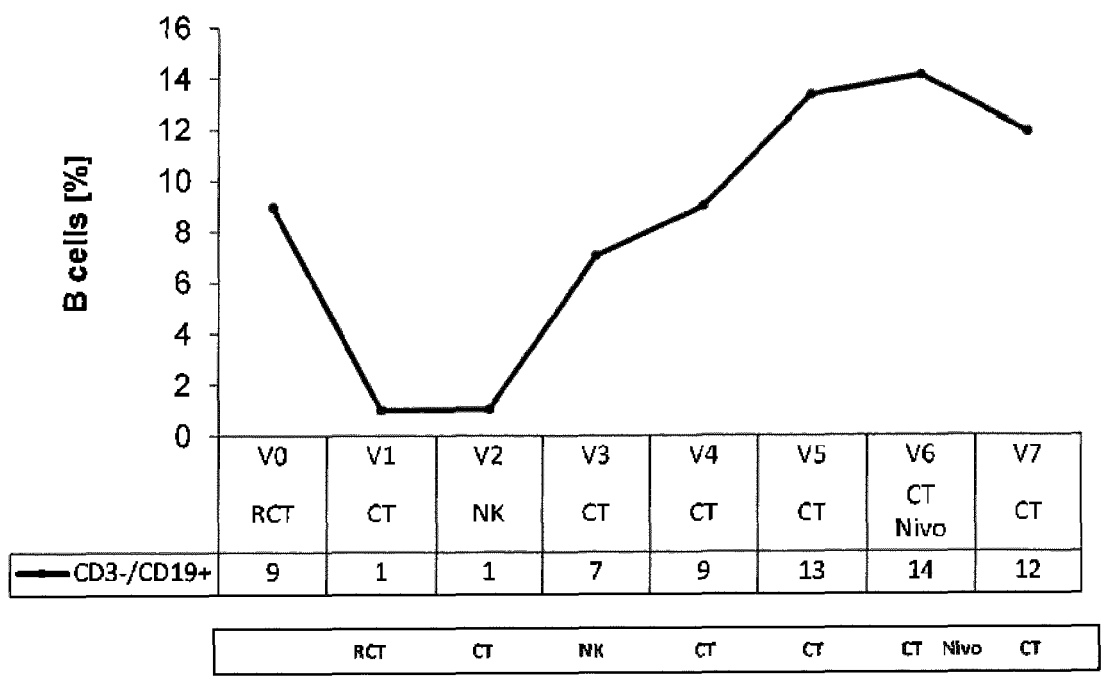
FIGS. 3A-F Percentage of different lymphocyte subpopulations at diagnosis, after therapy and in the follow-up period.

In view of the findings based on the clinical trial and analysis of immune cells of tumor patients subject in the trial illustrated in the Example, in a preferred embodiment of the present invention, the combination therapy is applied to a subject who received a conventional anti-tumor treatment or treatment of an infectious disease, wherein said treatment led to the depletion of B lymphocytes such as observed for the cisplatinum-based radiochemotherapy applied to the patient in the clinical trial. Put in other words, in one embodiment of the present invention the combination therapy is designed to be applied to a subject/patient who, compared to a corresponding normal control, i.e. healthy volunteer (100%) shows a substantial lower level of B cells, i.e. B lymphocytes ($CD3^-/CD19^+$), for example less than 90%-50%, typically less than 50% or even less than 20% of the normal level; see FIG. 3A.

It will be appreciated by the person skilled in the art that the components of the combination therapies of the present invention are typically provided in the form of one or more kits or pharmaceutical compositions, each containing a therapeutically-effective amount of the component(s) together with a pharmaceutically-acceptable buffer, excipient, diluent or carrier. Furthermore, depending on the route of administration, the Hsp70 based ingredient and/or further agent may be coated in a material to protect the ingredient from the action of acids and other natural conditions that may inactivate or denature the ingredient and/or agent. A pharmaceutical composition may include a pharmaceutically acceptable antioxidant. These compositions may also contain adjuvants such as preservatives, wetting agents, emulsifying agents and dispersing agents. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. Pharmaceutical compositions typically must be sterile and stable under the conditions of manufacture and storage. The composition can be formulated as a solution, microemulsion, liposome, nanoparticle or other ordered structure suitable to high drug concentration.

The Hsp70 based ingredient and the additional therapeutic agent used in the methods of the invention may each be provided as a separate pharmaceutical composition formulated together with a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible and are also compatible with the required routes of administration. Thus, the carrier for the Hsp70 based ingredient and the additional therapeutic agent may be suitable for systemic administration, which means administration into the circulatory system of the subject, including the vascular and/or lymphatic system. Such administration may be by any suitable route, but is typically parenteral. The phrase "parenteral administration" as used herein means modes of administration other than enteral and topical administration, and is typically achieved by injection, infusion or implantation. Suitable routes include intravenous, intramuscular, intradermal, intraperitoneal, subcutaneous, spinal or other parenteral routes of administration; see for review, e.g., international application WO 2016/023960 at page 39, section "Kits and pharmaceutical compositions" to page 48.

In one embodiment of the combination therapy for use according to the present invention, the immunomodulator is encapsulated in a carrier such as nanoparticles or liposomes, preferably wherein the carrier is linked or coated with said cmHsp70.1 antibody. Methods for preparing antibody-targeted immunocarriers for cancer treatment are known in the art; see, e.g., Shevtsov et al., Nanomedicine 12 (2016), 611-621; Shevtsov et al., Nanoscale 7 (2015), 20652-20664; and Bergs et al., Biochemica et Biophysica Acta (BBA)—Reviews on Cancer 1856 (2015), 130-143 for review.

It will be appreciated by the person skilled in the art that the presence of at least two active agents (as detailed above) may provide a synergistic benefit in the treatment of a tumor or infectious disease in a subject. The term "synergistic" includes that the therapeutic effect of the two agents in combination (e.g. as determined by reference to the rate of growth or the size of the tumor or duration/spread of the infection) is greater than the additive therapeutic effect of the two agents administered on their own or in such a distant regimen that influence on either treatment may be possible at all. Such synergism can be identified by testing the active agents, alone and in combination, in a relevant cell line model of the tumor or more preferably in an appropriate animal model. Preferably, the synergistic benefit includes an increase of the stimulation of the proliferation of NK cells, the cytolytic activity of NK cells and/or increase in the level of B cells, preferably wherein the cytolytic activity against tumor cells or infected cells of patients with infectious diseases is increased such as the cytolytic activity against leukaemia cells, lymphoma cells, tumor cells, metastasizing cells of solid tumors or cells of patients infected with viruses, bacteria and/or fungi.

Generally, in the combination therapy of the present invention, the combination of Hsp70 based pharmaceutical ingredient and the immunomodulator(s) are administered together in a single composition or administered separately in two or more different compositions or dosage forms. For example, the Hsp70 based pharmaceutical ingredient and the immunomodulator(s) are administered or contacted concurrently with, prior to, or subsequent to, the immunomodulator(s). In one embodiment of the combination therapy of the present invention, the method comprises
- (a) administering to the subject a therapeutically effective amount of the Hsp70 based pharmaceutical ingredient, preferably said peptide or activated PBMCs or fraction thereof, and currently or subsequently
- (b) administering to the subject a therapeutically effective amount of the immunomodulator.

In a preferred further embodiment, steps (a) and (b) are carried out simultaneously or subsequently wherein step (b) is carried out between 0 to 24 months after step (a), between 6 to 12 months after the last cycle of administration in step (a), preferably about 9 months after the last cycle of administration in step (a); and/or wherein step (a) is carried out between 1 week and 6 months after the subject had been treated by radiochemotherapy and/or received an equivalent therapy that leads to a reduced level of B cells, preferably about 1 to 4 months after the last cycle of RCT or like chemo- and/or radiotherapy. For an appropriate treatment regimen see also FIG. 1, which can of course be adapted to the subject in need thereof, for example taking the kind of tumor and stage of its progression into account.

In a particularly preferred embodiment, the combination therapy comprises (a) the peptide as defined in claim 2 in combination with IL-2 or NK cells activated by said peptide and IL-2, and (b) an inhibitor of an immune checkpoint molecule, preferably an anti-PD1 antibody; and optionally (c) Granzyme B, wherein the inhibitor of an immune checkpoint molecule is administered subsequent to said peptide in combination with IL-2 or activated NK cells.

As explained above and illustrated in the Example, after finishing the course of the treatment of a subject suffering from non-small cell lung carcinoma, a tumor positive for cell membrane Hsp70, with a Hsp70 based pharmaceutical ingredient, i.e. the TKD peptide ENKASTIM™ (synthetic peptide that mimics Hsp70), the subject was much better off than expected following the subsequent treatment of the subject with an inhibitor of an immune checkpoint molecule, i.e. an anti-PD-1 antibody. Therefore, without however intending to be bound by theory upon those observations, it is believed that a (pre)treatment of a patient suffering from a disease which is characterized by expression such as Hsp70 cell membrane-positive tumors and infectious diseases with an Hsp70 based pharmaceutical ingredient such as of the kind of TKD peptide ENKASTIM™ (synthetic peptide that mimics Hsp70) makes the subject more amenable to the treatment with common anti-tumor and anti-infectious agents which exert their effects on immune cells, in particular the cytolytic activity of NK cells. Thus, in a preferred embodiment of the combination therapy for use according to the present invention, the immunomodulator (b) is administered to the subject after completion of the treatment of the subject with the Hsp70 based pharmaceutical ingredient.

In view of the mentioned findings in accordance with the experiments described in the Example, in a further aspect the present invention relates to an anti-tumor or anti-infectious agent, preferably an immunomodulator as defined hereinbefore for use in treating or preventing relapse of a tumor or an infectious disease in a subject who received a treatment with the Hsp70 based pharmaceutical ingredient as defined above, preferably several cycles as illustrated in the Example and/or most preferably such that the level of B cells of the subject to be treated is normal and eventually recovered in/after the course of Hsp70 based treatment after lower levels of the B cells due to for example a previous standard care treatment such as RCT.

In principle, the combination therapy for use according to the present invention and the anti-tumor or anti-infectious agent may be designed for any suitable route of administration, including, but not limited to, intravenous, intratumoral, subcutaneous or intraperitoneal route. For example, in case of administration of an antibody (either or both the cmHsp70.1 antibody and antibody against a checkpoint molecule such as anti-PD-1 antibody) the method of treating or preventing relapse of a tumor or an infectious disease concerns the systemic, preferably intravenous administration of the antibody to a subject.

As illustrated in the Example, the combination therapy consisting of RCT, ex vivo Hsp70 activated NK cells and checkpoint inhibitor antibody Nivolumab is accompanied by a decrease in Hsp70 serum levels. Accordingly, both whether a tumor or infectious disease and the afflicted cells, respectively, are amenable to Hsp70 based combination therapy, the progress of the therapy can be monitored by assessing the level of membrane Hsp70 expressed by the disease in the patient. Therefore, in one embodiment of the combination therapy of the present invention prior to administration of at least one of said Hsp70 based pharmaceutical ingredient and immunomodulator(s) the presence and level of membrane Hsp70 expression on tumor cells or infected cells is determined in a sample from the patient, preferably wherein Hsp70 expression is determined using said cmHsp70.1 monoclonal antibody based tools and test systems, most preferably in serum of patients using a lipHsp70 ELISA or other assay based on the cmHsp70.1 monoclonal antibody; see the Example and international application WO 2016/120325, the disclosure content of which is incorporated herein by reference.

Regarding the disease to be treated by the combination therapy of the present invention, in principle any kind of disease in which the afflicted cells are characterized by the presence of Hsp70 on their cell surface/membrane or corresponding membrane expression can be induced will be amenable to such treatment, including solid tumor, metastatic tumor, cancer such as carcinomas of lung, colorectum, pancreas, larynx, stomach, peripheral and central nervous system including glioblastoma multiforme, head and neck, prostate, mammary, other carcinomas, sarcomas, chronic myeloic leukaemia (CML), acute myeloic leukaemia (AML), acute lymphatic leukaemia (ALL), non-Hodgkin Lymphoma (NHL), myeloproliferative syndrome (MPS), myelodysplastic syndrome (MDS), plasmocytoma, other leukemias, other malignant diseases, wherein Hsp70 is present on the surface of malignant cells, or the infectious disease has a viral, mycological or bacterial origin. In a particular preferred embodiment, the combination therapy of the present invention is applied to a subject suffering from, or having been treated for, non-small cell lung carcinoma (NSCLC).

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification, either by direct reference or numbering in parenthesis and listed separately. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention. A more complete understanding can be obtained by reference to the following specific Examples which are provided herein for purposes of illustration only and are not intended to limit the scope of the invention.

EXAMPLES

Example 1: Treatment of Lung Cancer as an Example of a Membrane Hsp70 Positive Tumor which is Amenable to the Combination Therapy Based on Hsp70 Based Pharmaceutical and an Immune Checkpoint Molecule Inhibitor Lung cancer is a major healthy burden worldwide with a mortality rate of more than 1.3 million per year [1]. Most lung cancer cases are non-small cell lung cancer (NSCLC, 85%) with squamous or non-squamous histology [2]. The overall (OS) and local progression-free survival (LPFS) of NSCLC patients in stage IIIB remains poor with less than 16 months [3]. One of the reasons for the high mortality of lung cancer is an advanced, non-curable disease stage at time of diagnosis. Patients in advanced tumor stages are treated with cisplatinum/vinorelbine based chemotherapy combined with local radiotherapy. Apart from direct cell-toxic effects, RCT has been found to mediate systemic inflammatory events that can mediate abscopal and/or bystander effects [4-7]. However, these immunostimulatory effects are extremely rare in clinical practice and an "inflammatory switchover" in the tumor microenvironment which is predominantly mediated by NF-κB, hypoxia inducible factor (HIF), and STAT might even initiate pro-survival signals for the tumor [8]. Therefore, a better understanding of radiation-induced immunomodulatory events is urgently needed.

An intact immune system consisting of active effector B, T, NKT and NK cells is able to recognize and kill tumor cells. However, a variety of immune escape mechanisms including anti-apoptotic factors, chronic tumor inflammation, immunosuppressive cell types and cytokines can limit the efficacy of anti-tumor immune responses [9-12] and eventually induce secondary cancers and metastases at a later stage [8]. A major "breakthrough" about 5 years ago was the identification and blockade of so-called immune checkpoint inhibitors that provide inhibitory feedback loops for immune cell mediated tumor rejection [13]. In healthy individuals, these immune checkpoints are needed to prevent autoimmunity, however, in case of cancer they can abrogate the cytolytic and migratory activity of effector T and NK cells against cancer. The PD-1 pathway is commonly used by lung cancer cells to avoid destruction by immune effector cells [14]. Therefore, inhibition of this pathway with an antibody against the PD-1 pathway could break immune tolerance towards cancer. Nivolumab a fully humanized IgG4 antibody targets PD-1 and thus attenuates inhibitory signals to enhance anti-cancer immunity [13, 15]. Nivolumab has been found to reactivate the immune system in many different tumor entities including lung cancer with impressive objective tumor responses [16, 17]. However, long-term benefits on OS have not yet been proven in clinical trials. This might be due to a low expression or absence of PD-1 on tumor cells, or by the lack of anti-tumor specific effector cells.

In accordance with the present invention, the effects of a therapeutic approach that combines standard care tumor treatment, i.e. RCT, tumor-specific Hsp70 activated NK cells therapy and immune checkpoint molecule inhibitor Nivolumab treatment in a patient with advanced squamous NSCLC had been investigated, resulted in the surprising observation that that the patient remained tumor-free by far over the median overall (OS) and local progression-free survival (LPFS) rate of NSCLC patients in stage IIIB; see Example 2.

In addition, the anti-tumor activity of the combined therapy consisting of pre-stimulated NK cells and PD-1 inhibition has been examined in a preclinical orthotopic glioblastoma animal model. In particular, mice with membrane Hsp70 positive glioblastoma were sham-treated or injected with ex vivo TKD/IL-2-activated NK cells and anti-PD-1 antibody either as a single regimen or a combined sequential therapy; see Example 3.

Patient and Methods
Ethics

Signed informed consent was obtained from the patient before start of the therapy and clinical protocol was approved by the institutional ethical review board of the Klinikum rechts der Isar, TU München (TUM), Munich. Germany.

Patient Characteristics

A 58-year old male was diagnosed with a histologically proven stage IIIB squamous non-small cell lung carcinoma (NSCLC, cT4, cN3, cM0) in November 2015. The tumor disease was confirmed by immunohistology and the size of the tumor was measurable by CT. The patient was in good clinical condition at the time of presentation (Karnofsky >90%). The tumor was strongly positive for p53, CK5/6, weakly positive for napsin A, negative for synaptophysin. Only 1.1% of the tumor cells showed a positivity for PD-L1, as determined by immunohistochemistry.

Treatment, Inclusion/Exclusion Criteria, Visits

As a first line therapy, the patient received 4 cycles of simultaneous cisplatinum/vinorelbin-based RCT from November 2015 until February 2016. The total irradiation dose was 64.8 Gy. One month after the end of RCT the patient received 4 cycles of ex vivo Hsp70 peptide TKD (2 µg/ml) plus low dose IL-2 (100 IU/ml) stimulated, autologous NK cells on a monthly basis (March 2016-June 2016). The patient fulfilled the following inclusion/exclusion criteria of an ongoing phase II clinical trial [18].

Inclusion Criteria:

First diagnosis of a histologically proven, unresectable squamous NSCLC in clinical stage IIIA/B, completion of RCT no longer than 8 months; progression-free according to "Response Evaluation Criteria in Solid Tumors" (RECIST 1.1) at first assessment after RCT; confirmed Hsp70 positivity as determined by lipHsp70 ELISA; male or female, age 18 to 75 years; ECOG stage <2; white blood cell counts >2.5×10$^9$/1, haemoglobin level >80 g/l, platelet counts >100×10$^9$/1 after completion of RCT; normal renal and liver function, and normal blood coagulation, written informed consent.

Exclusion Criteria

Antitumor treatments within 4 weeks prior to first dose of study medication, ALK-positivity or an activation of the EGFR-TK domain; metastatic tumor disease; other serious diseases, immunosuppressive drugs within 3 weeks before start of therapy, positive HIV-test, Hepatitis B, C, autoimmune diseases.

Restaging by computed tomography (CT) or positron-emission tomography (PET)/CT was performed regularly every 3 months after RCT and NK cell therapy in the first year.

Sixteen months after diagnosis (March 2017-April 2017) the patient received 3 cycles of the fully humanized IgG4 PD-1 immune checkpoint inhibitor antibody Nivolumab (Bristol-Myers Squibb, Princeton, NJ, USA; 3 mg/kg body weight, total dose 200 mg) as an intravenous infusion on a two-weekly basis. Blood samples for immunophenotyping was taken at study visits (V0-V7), and a PET-CT restaging was performed at V8:

V0 Diagnosis and recruitment into the study (November 2015)
V1 First restaging (CT) after RCT (February 2016)
V2: NK cell therapy (March 2016-June 2016)
V3-V5: Three restagings (CT) after NK cell therapy (June 2016, September 2016, November 2016)
V6: Restaging (CT) (February 2017) and Nivolumab therapy (March 2017 to April 2017)
V7: CT-guided bronchoscopy (May 2017)
V8: PET-CT (July 2017)

Hsp70 Peptide TKD, Ex Vivo Stimulation of NK Cells and Reinfusion

The 14-mer Hsp70 peptide TKD (aa 450-463 TKDNNLLGRFELSG) from the C-terminal domain of the major stress-inducible Hsp70 was used to stimulate patient-derived NK cells. The peptide TKD is the minimal essential sequence of Hsp70 protein to activate NK cells against membrane Hsp70 positive tumor cells. GMP-grade Hsp70 peptide was provided by Bachem (Bubendorf, Switzerland) at a purity of >96%.

Four weeks after RCT, leukocyte concentrates were obtained from the patient by a 3-4 h leukaphereses (Cobe Spectra, Heimstetten, Germany) at the University Hospital Regensburg, Germany. Peripheral blood lymphocytes (PBL) were isolated by density gradient centrifugation in a closed SEPAX system (Eysins, Switzerland) and then resuspended in CellGro SCGM Stem Cell Growth Medium (CellGenix, Freiburg, Germany). After counting, $5-10 \times 10^6$ cells PBL/ml CellGro medium were incubated with 2 µg/ml GMP-grade TKD peptide plus 100 IU/ml recombinant IL-2 (Proleukin, Novartis Pharma, Germany), transferred into 250 ml Teflon bags (Vue-Life-118, CellGenix, Freiburg, Germany), and cultured in an incubator (Heraeus, Nürnberg, Germany) under gentle rotation at 37° C., 5% v/v $CO_2$ in a humidified atmosphere (90% v/v) for 3-5 days in a GMP-laboratory (TUMCells). Thereafter, activated cells were harvested and washed twice and resuspended in Ringer's Lactate solution (500 ml) substituted with 0.1% w/v human serum albumin (HSA). Sterility testing of the cell product was performed before and after stimulation and before reinfusion. Within 24 h after stimulation with TKD/IL-2, autologous NK cells were reinfused to the patient by intravenous (i.v.) injection within 30-60 min using a stem cell reinfusion set. Tumor staging was performed either by CT, PET-CT, or CT-guided bronchoscopy.

Parameters and Flow Cytometric Analysis of Patient's Peripheral Blood Lymphocytes Routine laboratory parameters (differential blood counts, haemoglobin, white blood cell counts) blood chemistry (Creatinine, AST/SGOT, ALTSGPT, G-GT, LDH) were determined after each therapy (RCT, NK cell and Nivolumab therapy) and every three months in the follow-up period. The following lymphocyte subpopulations were measured by flow cytometry on a FACSCalibur™ instrument (BD Biosciences San Jose, CA, USA) in ex vivo cell cultures before and after stimulation and in the peripheral blood of the patient at the different visits (V0-V7): $CD3^-/CD19^+$ B cells, $CD3^+$ T cells, $CD3^-/CD4^+$ helper T cells, $CD3^+/CD8^+$ cytotoxic T cells, $CD3^-/CD56^+$ NKT cells, $CD3^-/CD56^+$ NK cells, $CD3^-/CD94^+$ NK cells, $CD3^-/NKG2D^+$ NK cells, $CD3^-/NKp30^+$, $NKp44^+$, $NKp46^+$ NK cells. The combinations of fluorescently-labeled antibodies used for flow cytometry are summarized in Table 1.

Measurement of Plasma/Serum Hsp70 Levels

Blood was taken in EDTA (EDTA K/9 ml tubes, S-Monovette, Sarstedt, Nürnbrecht, Germany) and serum tubes (S-Monovette 7.5 ml Z, Sarststedt, Nürnbrecht, Germany) at diagnosis, before start and after each therapy and every three months during the follow-up period. After centrifugation for 10 min at 300 g, plasma and serum aliquots of 100 to 300 µl were prepared and directly stored at −80° C. for further analysis. Hsp70 serum/plasma concentrations were determined using the lipHsp70 ELISA and the sandwich ELISA kit (Duo Set IC; R&D Systems) according to the manufacturer's instructions. The lipHsp70 ELISA is able to detect both lipid-bound and free Hsp70 quantitatively by using cmHsp70.1 monoclonal antibody [20], as detection antibody, whereas the R&D ELISA predominantly detects free Hsp70. Briefly, 96-well MaxiSorp Nunc-Immuno plates (Thermo Fisher, Rochester, NY, USA) were coated overnight with 2 µg/ml rabbit polyclonal antiserum (Davids, Biotechnology, Regensburg, Germany) directed against human Hsp70 in sodium carbonate buffer (0.1 sodium carbonate, 0.1 M sodium hydrogen carbonate pH 9.6). After three washing steps in PBS (Life Technology, Carlsbad, CA, USA), 0.05% v/v Tween 20 (Calbiochem, Merck, Darmstadt, Germany) and a blocking step with 2% w/v skimmed milk powder (Carl Roth, Karlsruhe, Germany), plasma/serum samples were added to each well at a dilution of 1:5 in Crossdown buffer. After another washing step, biotinylated murine anti-human cmHsp70.1 mAb (multimmune, Munich, Germany) was added at a concentration of 4 µg/ml. Following the chromogenic reaction using horseradish peroxidase-conjugated streptavidin (Pierce, Thermo, Rockford, IL, USA), absorbances were measured in a Microplate ELISA reader (BioTek, Winooski, VT, USA) at 450 nm, corrected by absorbance at 570 nm. Each sample was measured in duplicates in three independent experiments using an eight point standard curve with recombinant Hsp70 protein diluted in Crossdown buffer (0-50 ng/ml), as a reference.

TABLE 1

Antibody panel and combinations used for phenotypic characterization of lymphocytes

| Cell Type | Antibody | Company | Cat. No. | Volume (µl) |
|---|---|---|---|---|
| Ctrl | IgG1-FITC | BD | 345815 | 5 |
|  | IgG1-PE | BD | 345816 | 5 |
|  | IgG1-PerCP | BD | 345817 | 5 |
|  | IgG1-APC | Caltag/Invitrogen | MG 105 | 1 |
| T/NK | CD94-FITC | BD | 555888 | 5 |
|  | CD56-PE | BD | 345811 | 5 |
|  | CD3-PerCP | BD | 345766 | 10 |
|  | CD45-APC | Caltag/Invitrogen | MHCD 4505 | 1 |
| B/T/NK | CD56-FITC | BD | 345811 | 5 |
|  | CD19-PE | BD | 555413 | 20 |
|  | CD3-PerCP | BD | 345766 | 10 |
|  | CD45-APC | Caltag, Invitrogen | MHCD 4505 | 1 |
| T/NK | CD56-FITC | BD | 345811 | 5 |
|  | CD16-PE | BD | 555407 | 10 |
|  | CD3-PerCP | BD | 345766 | 10 |
|  | CD45-APC | Caltag/Invitrogen | MHCD 4505 | 1 |

TABLE 1-continued

Antibody panel and combinations used for phenotypic characterization of lymphocytes

| Cell Type | Antibody | Company | Cat. No. | Volume (μl) |
|---|---|---|---|---|
| T/NK | CD56-FITC | BD | 555518 | 5 |
|  | NKG2D-PE | R&D | FAB139P | 10 |
|  | CD3-PerCP | BD | 345766 | 10 |
|  | CD69-APC | BD | 340560 | 5 |
| T/NK | CD56-FITC | BD | 345811 | 5 |
|  | NKp30-PE | BC | PN IM 3709 | 10 |
|  | CD3-PerCP | BD | 345766 | 10 |
|  | CD69-APC | BD | 340560 | 5 |
| T/NK | CD56-FITC | BD | 345811 | 5 |
|  | NKp46-PE | BC | PN IM 3711 | 10 |
|  | CD3-PerCP | BD | 345766 | 10 |
|  | CD69-APC | BD | 340560 | 5 |
| T/NK | CD94-FITC | BD | 555888 | 5 |
|  | NKG2D-PE | R&D | FAB139P | 10 |
|  | CD3-PerCP | BD | 345766 | 10 |
|  | CD56-APC | BD | 555518 | 10 |
| T/NK | CD94-FITC | BD | 555888 | 5 |
|  | NKp30-PE | BC | PN IM 3709 | 10 |
|  | CD3-PerCP | BD | 345766 | 10 |
|  | CD56-APC | BD | 555518 | 10 |
| T/NK | CD94-FITC | BD | 555888 | 5 |
|  | NKp46-PE | BC | PN IM 3711 | 10 |
|  | CD3-PerCP | BD | 345766 | 10 |
|  | CD56-APC | BD | 555518 | 10 |
| CD4/CD8 T | CD4-FITC | BD | 555346 | 20 |
|  | CD8-PE | BD | 555366 | 20 |
|  | CD3-PerCP | BD | 345766 | 10 |
|  | CD45-APC | Caltag/Invitrogen | MHCD 4505 | 1 |
| Ctrl | IgG1-FITC | BD | 345815 | 5 |
|  | IgG1-PE | BD | 345816 | 5 |
|  | IgG1-PerCP | BD | 345817 | 5 |
|  | IgG1-APC | Caltag/Invitrogen | MG 105 | 1 |
| CD4 Treg | CD4-FITC | BD | 555346 | 20 |
|  | FoxP3-PE | BD | 560046 | 20 |
|  | CD3-PerCP | BD | 345766 | 10 |
|  | CD25-APC | BD | 340907 | 5 |

Abbreviations: BD, BD Biosciences; BC, Beckmann Coulter

Statistics

Statistical analysis was performed using the Student's t-test.

Immunohistochemistry

For immunohistochemistry formalin-fixed, paraffin-embedded (FFPE) specimens were cut at 4 μm and transferred onto slides. All staining procedures were automatically performed on a Ventanas Benchmark XT.

Orthotopic Injection of GL261 Glioblastoma Cells into C57Bl/6 Mice GL261 mouse glioblastoma cells with high membrane Hsp70 expression [46], obtained from the Russian Cell Culture Collection, are cultured in DMEM medium supplemented with 10% heat-inactivated fetal calf serum (FCS), 2 mM L-glutamine and antibiotics (100 IU/ml Penicillin G and 100 μg/ml Streptomycin) at 37° C. with 6% $CO_2$. C57Bl/6 mice were purchased from the animal nursery "Rappolovo" of the Russian Academy of Medical Science (St. Petersburg, Russia). All animal experiments are approved by the local ethical committee of Pavlov First St. Petersburg State Medical University and were in accordance with institutional guidelines for the welfare of animals. Briefly, 10-week old female C57BL/6 mice were anesthetized by ip injection with 10 mg Zoletyl-100 (Vribrac Sante Animale, Carros, France) and 0.2 ml 2% Rometar (Bioveta, Ivanovice, Czech Republic) before mounting them in a stereotactic frame (David Kopf Instruments, Tujunda, CA, USA). GL261 cells ($1 \times 10^5$) resuspended in sterile PBS (5 μl) were stereotactically injected into the nucleus caudatus dexter of anesthetized mice.

Ex Vivo Stimulation of Mouse NK Cells with TKD/IL-2

Peripheral blood lymphocytes (PBLs) were isolated of sacrificed C57BL/6 mice by Ficoll gradient centrifugation. After separation, PBL were resuspended in RPMI-1640 supplemented with 2 mM L-glutamine, 10% FBS, and antibiotics (100 IU/ml Penicillin G and 100 μg/ml Streptomycin). Previous data have indicated that NK cell activation is superior when, instead of purified NK cells, PBL are stimulated with the 14-mer TKD peptide (TKDNNLLGRFELS, 2 μg/ml, Bachem, Bubendorf, Switzerland) and IL-2 (100 IU/ml) at cell densities of $5-10 \times 10^6$ PBL/ml for 3-4 days [47,48]. Since the human TKD sequence differs only in one amino acid from that of mice (TKDNNLLGRFELSG and TRDNNLLGRFELSG) mouse NK cells can be stimulated with the human TKD peptide sequence [20].

Treatment of Glioblastoma in Mice

For comparing the efficacy of singular or combined therapies consisting of an adoptive transfer of ex vivo TKD/IL-2-stimulated NK cells and anti-PD-1 immune checkpoint inhibitor antibody (RMP1-30, eBioscience, Frankfurt/Main, Germany) animals with comparable tumor sizes (according to MRI volumometrics) were randomly divided into 5 groups (8 animals per group): Animals of the control groups were injected either with 100 μl PBS (iv) or with 500 μl isotype-matched IgG antibody (ip) on days 6, 9, 12 and 15. Animals of the treatment groups were iv injected either with NK cells ($6 \times 10^6$ in 100 μl PBL) on days 6, 9, and 12 and/or ip injected with anti-PD-1 antibody on days 6 (500 μg), 9 (250 μg), 12 (250 μg) and 15 (250 μg) in a volume of 500 μl PBS.

Magnetic Resonance (MR) Tumor Imaging of Mouse Glioblastoma

Tumor progression was assessed before and after each therapy on days 5, 10, 15, 20, 25 and 30 using a high-field 11.0 T MR scanner (Bruker, Bremen, Germany) with a customized rodent coil. High-resolution anatomical T2-weighted scans (repetition time [TR]/echo time [TE] 4200/36 ms, flip angle 180°, slice thickness 1.0 mm, interslice distance 1.2 mm, field of vision (FoV) 3.0×3.0 cm, matrix 256×256, in total 20 slices) were performed in coronal planes. Additionally, T1-weighted scans (TR/TE 1500/7.5 ms, flip angle 180°, slice thickness 1.0 mm, FoV 3.0×3.0 cm, matrix 256×256), FLASH scans (TR/TE 350/5.4 ms, flip angle 40°, slice thickness 1.0 mm, 3.0×3.0 cm, matrix 256×256) in coronal planes were performed. The obtained images were analyzed using adequate software (AnalyzeDirect Inc, Overland Park, KS, USA).

Mouse Tumor Immunohistochemistry (IHC)

Animals were anesthetized by ip injection of 150-200 mg/kg pentobarbital. After perfusion with 100 ml saline/4% paraformaldehyde, whole brains were removed and tumor volumes were assessed. Tissue was fixed in 4% paraformaldehyde/30% sucrose, embedded in Tissue-Tek® and blocks were cut into serial sections (5-7 μm). $CD8^+$ T cells, NK1.1+ cells and PD-1+ lymphocytes were stained on IHC sections using anti-CD8 (53-6.7, Biolegend, San Diego, CA, USA), anti-NK1.1 (PK136, Biolegend, San Diego, CA, USA) and anti-PD-1 (RMP1-30, eBioscience, Frankfurt/Main, Germany) antibodies according to an established protocol. Tumor-infiltrating $CD8^+$ T cells, NK1.1 cells and $PD-1^+$ cells were counted in 3 fields of views by two independent researchers.

Statistics

The software program Statistica Version 9.2 was employed for statistical analysis of animal data. Survival of the mice was determined using Kaplan-Meier analysis. The Student's t-test was used to determine differences in the percentage of infiltrating lymphocytes. In all experiments, differences were considered as being statistically significant at a value p<0.05.

Example 2: Combined Therapy of Hsp70 Based Ingredient and Checkpoint Molecule Inhibitor is Well Tolerated and Results in Long-Term Tumor Control Membrane-bound heat shock protein 70 (Hsp70) serves as a tumor-specific recognition structure for Hsp70-peptide TKD plus IL-2 activated natural killer (NK) cells. Cellular stress including radiochemotherapy (RCT) has been found to increase the membrane expression of Hsp70 on tumor cells. Safety and feasibility of ex vivo TKD/IL-2 activated, autologous NK cells have been demonstrated in a phase I clinical trial. In accordance with the present invention, the immunostimulatory activity of a combined therapy consisting of RCT, NK cells and immune checkpoint inhibitor antibody Nivolumab has been studied in a patient with membrane Hsp70 positive squamous non-small lung cell carcinoma (NSCLC).

Clinical Response and Patient's Clinical History

Figure 2:
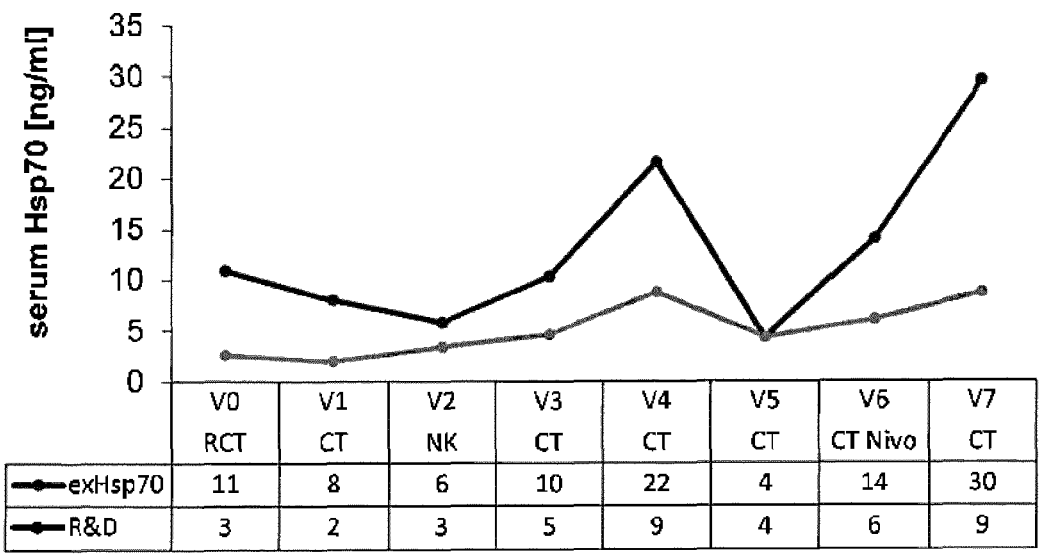
FIG. 2: Hsp70 serum levels at diagnosis (V0), after RCT (V1), after CT-guided restaging (V2), after 4 cycles of NK cell therapy (V3), after 3-monthly CT-guided restaging (V4-V6), after 3 cycles of Nivolumab treatment (V7), as determined by the R&D Hsp70 ELISA and the lipHsp70 ELISA.

A 58-year old male smoker patient was diagnosed in November 2015 with intermediate-differentiated, non-operable squamous NSCLC (cT4, cN3, cM0, stage IIIB). The clinical history, study design, visits and dates of therapies of the patient are summarized schematically in FIG. 1. Elevated exosomal Hsp70 (exHsp70) serum levels (11 ng/ml, FIG. 2) above a threshold of 6 ng/ml, as determined by the lipHsp70 ELISA [19], were indicative for an Hsp70 membrane-positive tumor phenotype at diagnosis (V0). Following simultaneous RCT, a partial tumor response was detected by CT-scanning (V1). The decrease in tumor size induced by RCT was accompanied by a lowering of exHsp70 from 11 to 8 ng/ml. In contrast, the amount of free Hsp70 which predominantly originates from dying tumor cells, as measured by the R&D ELISA, remained stable between V0 and V3, but increased between V2 and V7 (FIG. 2). Four weeks after RCT the patient received 4 cycles of ex vivo TKD/IL-2 stimulated, autologous NK cells (V2) by i.v. injection every following month which was accompanied by a further reduction of the exHsp70 serum levels to 6 ng/ml. The number of ex vivo stimulated, re-infused total lymphocytes and NK cells increased from $1.2$-$3.5 \times 10^9$ and $1.7$-$5.3 \times 10^8$, respectively, between the first and third reinfusion cycle (Table 2). The viability rate of the infused lymphocytes was always above 92%.

TABLE 2

Number of re-infused total white blood cells (WBC), total lymphocytes, total CD3⁻/CD56⁺ NK cell counts, percentage of lymphocytes and CD3⁻/CD56⁺ NK cells at reinfusion cycle 1 to 4. Viability of the reinfused apharesis product was above 92%.

| Cycle | 1. | 2. | 3. | 4. |
|---|---|---|---|---|
| WBC (×10⁹) | 1.2 | 2.8 | 3.8 | 3.2 |
| Total lymphocytes (×10⁹) | 1.2 | 2.5 | 3.5 | 2.9 |
| Total CD3⁻/CD56⁺ NK cells (×10⁸) | 1.7 | 3.5 | 5.3 | 4.0 |
| Lymphocytes (%) | 97 | 90 | 92 | 89 |
| CD3⁻/CD56⁺ NK cells (%) Normal: 5-35 | 14 | 14 | 15 | 14 |

A CT-based restaging three month after NK cell therapy (V3) revealed a further tumor regression, although exHsp70 serum levels started to increase. Since this increase occurred only transiently between V3 and V4 when CRP values were also found to be elevated it was assumed that high serum Hsp70 values are caused by inflammation rather than by tumor growth. One year after the start of RCT (V5), an increased cell density in the right central tumor area was determined by CT-scanning. Despite no signs of distant metastasis and decreasing Hsp70 serum levels the patient was treated with the immune checkpoint inhibitor antibody Nivolumab, as a second line therapy. After 3 cycles with Nivolumab, no increase in tumor size (V6) and an inflammatory induced increase in Hsp70 serum levels was detected. A histological restaging of a CT-guided bronchoscopy revealed no signs of viable tumor cells 18 months after diagnosis (V7), but a high infiltration of immune effector cells within necrotic tumor tissue. The following PET-CT based restaging 21 months after diagnosis also revealed no tumor progress and no distant metastasis (V8). The last CT scan was performed 32 months after diagnosis without showing tumor progression.

Apart from a transient increase in C-reactive protein (CRP) as an indicator for inflammation between V3 and V4 and after V6, routine laboratory parameters, such as differential blood counts, haemoglobin, white blood cell counts, creatinine, aspartate aminotransferase (AST), alanine aminotransferase (ALT), gamma glutamine transferase (γ-GT), lactate dehydrogenase (LDH) remained within normal levels throughout the therapeutic intervention and follow-up period.

Phenotypic Characterization of Patient Derived Effector Cells

In addition to the Hsp70 serum levels, the composition of major lymphocyte subpopulations was determined at diagnosis before, during and after therapy at visits V0-V7. As summarized in FIG. 3A, the fraction of B cells which was already below normal levels at diagnosis, dropped further during RCT until one month after RCT, but recovered up to initial levels during the adoptive transfer of ex vivo stimulated autologous NK cells. Interestingly, the percentage of B cells further increased above initial levels at diagnosis within the follow-up period (V3-V6). After 3 treatment cycles with Nivolumab (V6), the fraction of B cells slightly dropped, but remained above initial levels at V0. In conclusion, B cells show a faster recovery from radiation-induced damage following the adoptive transfer of NK cells and increase to normal or even above initial levels in the follow-up period. A substantial and rapid recovery of the B cell compartment might partly explain the observed beneficial clinical outcome of the patient.

Figure 3B:
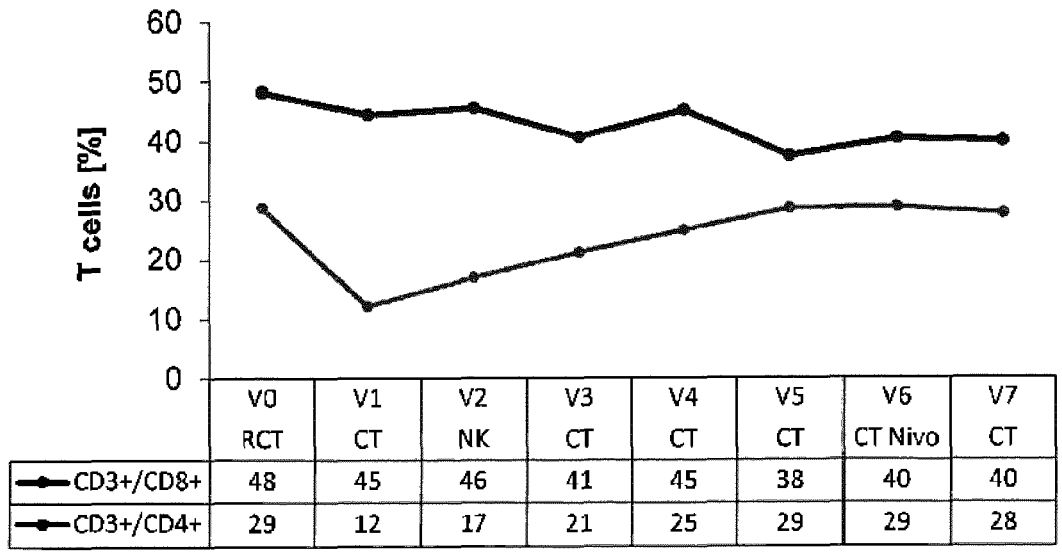

With respect to the major T cell subsets, the patient already exhibited higher percentages of $CD8^+$ cytotoxic T cells compared to $CD4^+$ helper T cells at diagnosis (V0). In contrast, healthy individuals generally have higher percentages of $CD4^+$ (40-60%) compared to $CD8^+$ (20-40%) T lymphocytes. After RCT (V1), the percentage of $CD4^+$ T cells dropped transiently but reached initial levels after NK cell therapy (V3, FIG. 3B). The percentage of $CD8^+$ cytotoxic T lymphocytes remained stably higher than that of $CD4^+$ T cells during the whole course of therapies and in the follow-up period. The treatment with the immune checkpoint inhibitor antibody Nivolumab had no effect on the percentage of $CD4^+$ or $CD8^+$ T cells, when measured 2 months after therapy. In summary, persistently elevated levels of $CD8^+$ cytotoxic T cells might elicit protective anti-tumor immunity.

Figure 3C:
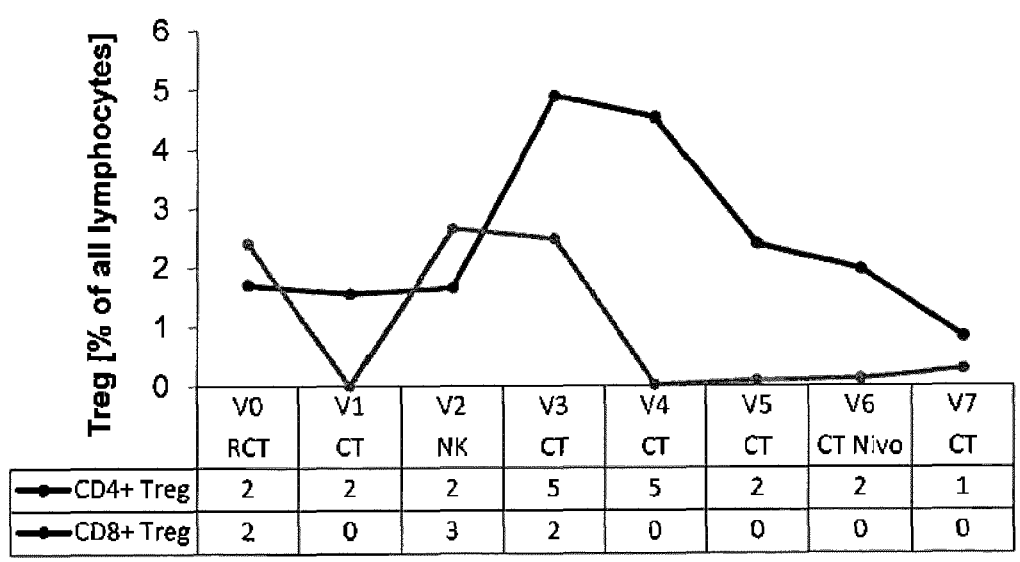

The $CD8^+$ T cell mediated antitumor immunity might further profit from a drop in the prevalence of immunosuppressive/immunoregulatory $CD4^+$ and $CD8^+$ T (Treg) cells which is induced by the Nivolumab treatment (FIG. 3C). The transient increase in Treg cells after RCT and NK cell therapy (V3) might be explained by the inflammation-induced release of the pro-inflammatory cytokine IL-2. However, a comparison of the percentage of Treg cells at V0 and V7 revealed a reduction of approximately 50% which might be due to the immunomodulatory effects of NK cell therapy and immune checkpoint inhibitor blockade.

Figure 3D:
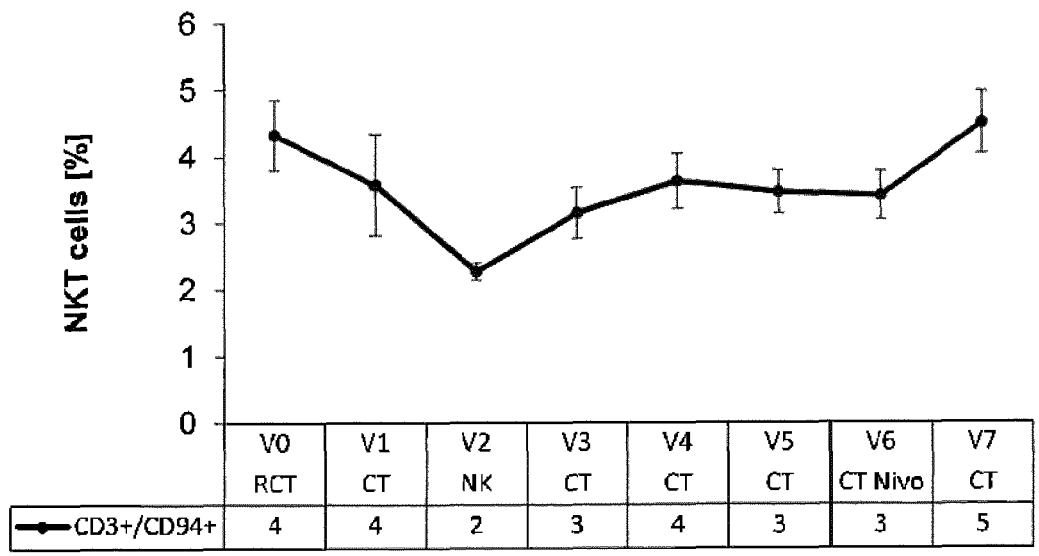

RCT induces a significant decrease in $CD3^+/CD94^+$ NKT cells ($p<0.05$) which recovers to initial levels upon NK cell therapy and Nivolumab treatment, as shown in FIG. 3D. Since NKT cells also can exert antitumor activities this increase might support antitumor immune responses.

Figure 3E:
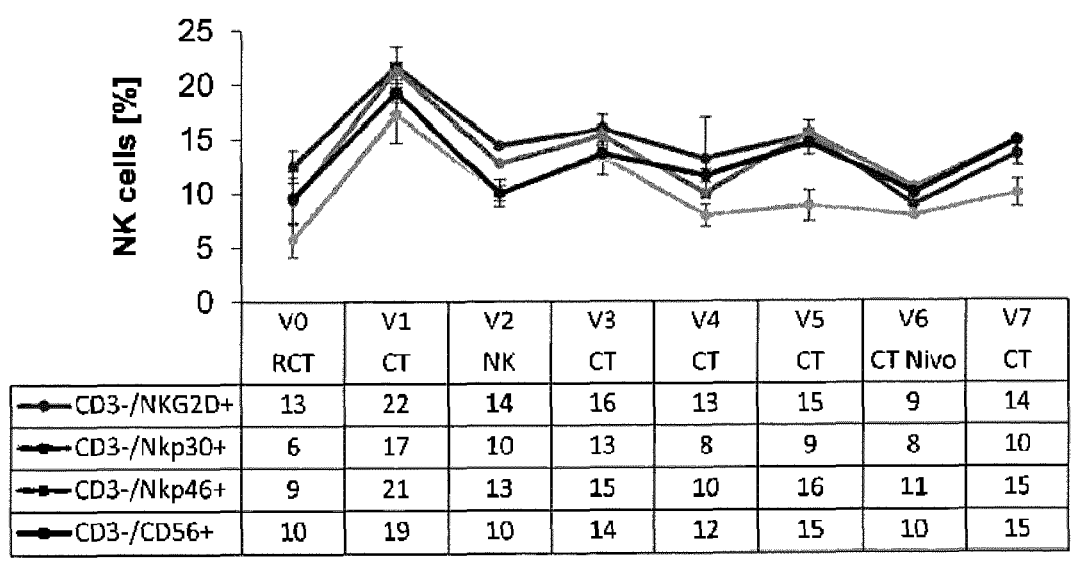

As shown in FIG. 3E, the percentage of nearly all $CD3^-$ NK cell subsets such as $CD3^-/NKG2D^+$, $CD3^-/Nkp30^+$, $CD3^-/Nkp46^+$, $CD3^-/CD56^+$ remained nearly unchanged within the normal range (between 5 and 20%) during the whole course of therapies and in the follow-up period. This finding might be due to elevated intracellular levels of glutathione in NK cells compared to T cells that make NK cells more resistant to therapies. Due to potential immunostimulatory effects caused by RCT, a slight upregulation of the percentage of all NK cell subtypes which failed statistical significance was observed between V0 and V1.

Figure 3F:
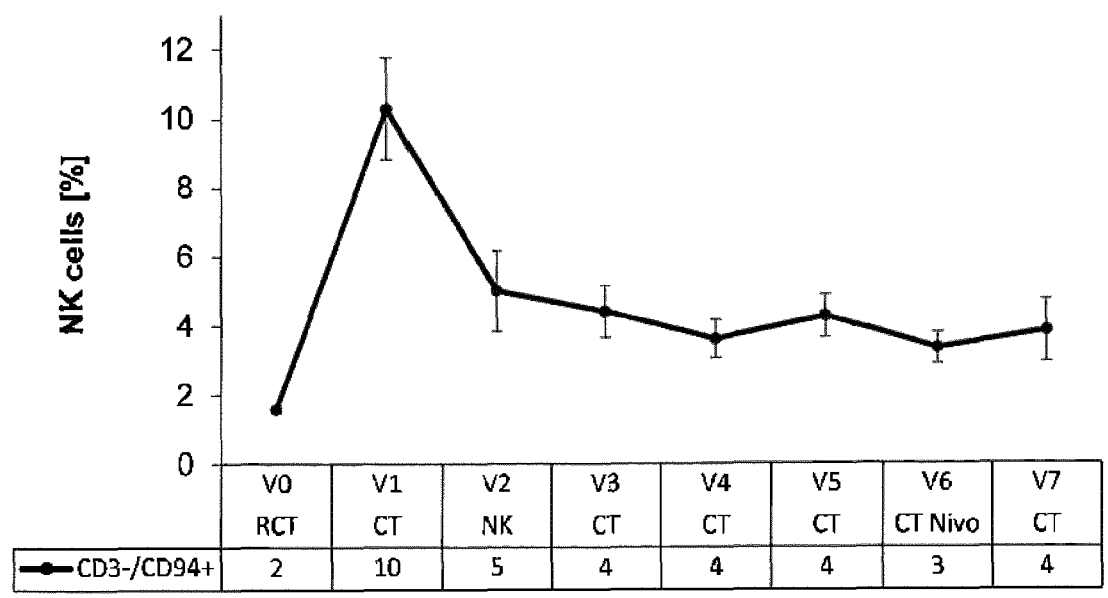
Figure 4:
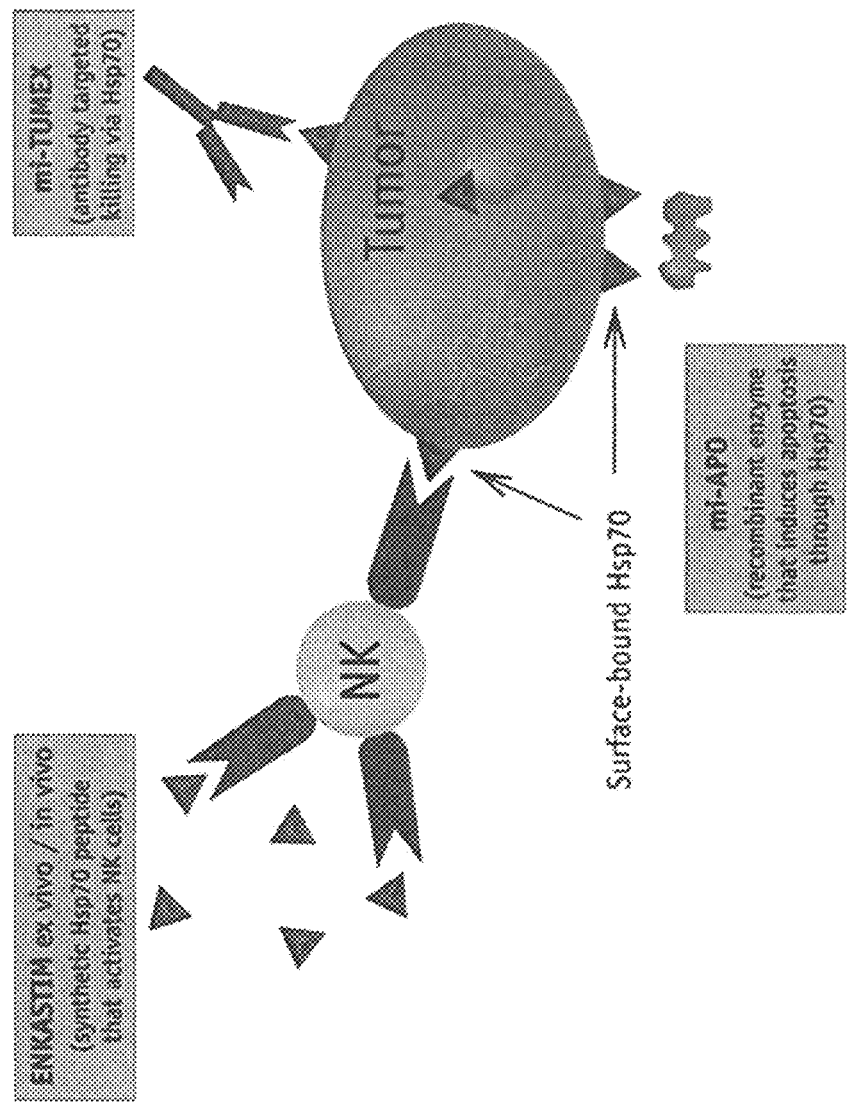
FIG. 4: Illustrates heat shock protein 70 (Hsp70) based pharmaceutical ingredients, i.e. compounds derived from or targeting the membrane-expressed form of Hsp70. Membrane Hsp70 is most frequently expressed on a variety of different tumor types including lung, colon, breast, head and neck, stomach, pancreas carcinomas, malignant melanoma, central nervous system including glioblastoma multiforme and hematological diseases, but never on the corresponding normal tissues. In addition to tumors, infected cells present even higher amounts of Hsp70 on their surface membranes.

The subtype of $CD3^-/CD94^+$ NK cells which are assumed to have the capacity to kill Hsp70 membrane positive tumor cells ranged below 2% at diagnosis (V0), increased significantly after RCT and reached normal levels after adoptive NK cell transfer (FIG. 3F). The drastic increase in NK cells after RCT might be due to immunostimulatory, abscopal effects induced by RCT-induced tumor cell death. Following adoptive transfer of activated NK cells the composition of NK cell subpopulations remained unaltered because ex vivo stimulation does not induce NK cell growth but rather induces an increase in the density of expression of activatory NK cell receptors per cell [22]. Furthermore, the therapy with the immune checkpoint inhibitor Nivolumab does not appear to alter the composition of NK cell subsets but enable them to regain their killing activity against tumor cells.

Exosomal and Free Hsp70 Serum Levels as Prognostic Markers

Levels of exosomal Hsp70 (exHsp70) in the blood of tumor patients have been shown to predict viable tumor mass in tumor-bearing mice and patients with NSCLC [24]. In contrast, free Hsp70 in the blood of patients predominantly originates from dying cells as a response to therapy or inflammation. Herein, free and lipid-bound Hsp70 were measured using two different Hsp70 ELISAs, the R&D Systems ELISA (Bio-Techne GmbH, Wiesbaden-Nordenstadt Germany) that predominantly detects free Hsp70 and the lipHsp70 ELISA The latter quantitatively detects both forms of Hsp70 in the serum and plasma with a high precision, whereas the R&D ELISA only detects free Hsp70 with a much lower precision. The recovery rate of spiked free Hsp70 in serum and plasma is below 5% with the R&D Systems ELISA but greater than 85% with the lipHsp70 ELISA [19].

As shown in FIG. 2, the levels of free Hsp70, detected by the R&D Systems ELISA gradually increased from V0-V7, whereas Hsp70 levels measured by the lipHsp70 ELISA decreased after RCT (V1), transiently increased during and after NK cell therapy (V4) and dropped thereafter (V5). The drop in exHsp70, as determined by the lipHsp70 ELISA, after RCT is associated with a reduction in viable tumor mass, whereas the transient increase thereafter could be due to a RCT and NK cell therapy-induced inflammation which causes the release of free Hsp70. The upregulation of the Hsp70 serum levels measured by the lipHsp70 ELISA are associated with increased CRP values, whereas the downregulated levels are associated with a decrease in viable tumor mass. The break of immunotolerance by Nivolumab therapy also induces inflammation which, in turn, enhances serum Hsp70 levels.

Example 3: Combined Therapy of Hsp70 Based Ingredient and Checkpoint Molecule Inhibitor Results in Long-Term Tumor Control which is Accompanied by a Massive Immune Cell Infiltration in a Preclinical Glioblastoma Model In Example 3, the sequential treatment of glioblastoma (GL261)-bearing mice with Hsp70 activated NK cells and anti-PD-1 antibody is shown to significantly enhance Overall Survival (OS) and induce immune cell infiltration. The effects of a singular or combined treatment consisting of ex vivo TKD/IL-2-stimulated NK cells (NK) and immune checkpoint inhibitor blockade against PD-1 (PD-1) were determined in mice with membrane Hsp70 positive orthotopic glioblastomas (GL261) [46]. The most rapid tumor growth was observed in sham-treated (PBS, IgG isotype-matched antibody) control mice, as determined by MRI scanning. On day 10 day, tumors reached a volume of 179±12 mm$^3$ (PBS) and 203±12 mm$^3$ (IgG, Table 3), and all mice of the control groups died before day 15.

TABLE 3

Tumor volumes (mm³) of mice (n = 8 per group) of control (ctrl)
and treatment groups (NK, PD-1, NK + PD-1). Sham treatment:
PBS (ctrl, 100 µl, iv), IgG (ctrl, 500 µl, ip) isotype-matched
control antibody; treatment: NK, ex vivo TKD/IL-2-activated NK cells
(6 × 10⁶ cells in 100 µl PBS, iv); PD-1 antibody (500 µl, ip); NK + PD-1,
ex vivo activated NK cells (6 × 10⁶ cells in 100 µl PBS, iv) + PD-1 (500 µl, ip)
antibody over 6 time points (days 5, 10, 15, 20, 25, 30). The data are mean values ± SD.

|  | Day 5 | Day 10 | Day 15 | Day 20 | Day 25 | Day 30 |
|---|---|---|---|---|---|---|
| PBS (ctrl) | 29 ± 3 | 179 ± 12 | | | | |
| IgG (ctrl) | 27 ± 10 | 203 ± 12 | | | | |
| NK cells | 23 ± 5 | 66 ± 11 | 104 ± 31 | 203 ± 33 | | |
| PD-1 antibody | 28 ± 15 | 47 ± 9 | 80 ± 18 | 101 ± 24 | 205 ± 24 | |
| NK cells + PD-1 antibody | 27 ± 8 | 45 ± 8 | 57 ± 10 | 73 ± 10 | 87 ± 9 | 124 ± 22 |

Three iv injections of TKD/IL-2-activated NK cells, or 4 ip injections of anti-PD-1 antibody caused a significant tumor growth delay, the maximum tumor volume of 203±33 and 205±24 mm³ was reached 10 and 15 days later than in the sham-treated control group (Table 3). The best therapeutic outcome however, was achieved after a sequential treatment with NK cells and PD-1 antibody. Even on day 30, the size of the tumors of 4 mice was only 124±22 mm³, and 4 out of 8 mice treated with the combined therapeutic approach showed a complete tumor control (Table 3).

As shown by Kaplan-Meier analysis, the OS of mice treated either with NK cells (3 injections, iv) or anti-PD-1 antibody (4 injections, ip) was significantly higher (p<0.05) than that of sham-treated mice (PBS, 3 injections, iv; IgG, 4 injections, ip). It appeared that 4 treatment cycles with PD-1 antibody are slightly more efficient than 3 cycles of pre-activated NK cells with respect to OS. Due to the iv route, the number of NK injections was limited to 3 cycles.

The best therapeutic outcome was observed in mice after a combined, sequential treatment. The OS of these mice was significantly higher than that of the sham-treated control groups (p<0.001) and that of mice treated with NK cells or PD-1 antibody (p<0.05). In line with these findings, the number of tumor-infiltrating CD8⁺ T and NK1.1 cells in tumor sections of mice treated with NK cells and PD-1 antibody was significantly higher than in the control group (p<0.05), and in the group of mice treated either with NK cells or PD-1 antibody alone (p<0.05; Table 4).

TABLE 4

Number of tumor-infiltrating CD8⁺ T cells, NK1.1 cells and PD-1⁺
expressing effector cells in tumor sections of mice of the sham-treated
control (ctrl) and treatment groups (NK, PD-1, NK + PD-1). Sham-
treated groups: PBS (ctrl), PBS (100 µl, iv), IgG (ctrl), isotype-matched
IgG control antibody (500 µl, ip). Treated groups: NK, ex vivo
activated NK cells (6 × 10⁶ cells in 100 µl PBS, iv), PD-1,
PD-1 antibody (500 µl, ip), NK + PD-1, ex vivo activated NK cells
(6 × 10⁶ cells in 100 µl PBS, iv) + PD-1 antibody (500 µl, ip).
Data are mean values of three fields of view ± SD.
Values that differ significantly (p < 0.05) from PBS and IgG control
groups are marked with an asterisk (*)

|  | NK1.1 cells | CD8⁺ T cells | PD-1⁺ cells |
|---|---|---|---|
| PBS (ctrl) | 7 ± 4 | 6 ± 2 | 54 ± 10 |
| IgG (ctrl) | 5 ± 1 | 8 ± 1.5 | 54 ± 5 |
| PD-1 antibody | 30 ± 8* | 17 ± 3* | 17 ± 4* |
| NK cells | 20 ± 8* | 15 ± 4* | 35 ± 5* |
| NK cells + PD-1 antibody | 40 ± 5* | 22 ± 4* | 13 ± 6* |

The number of tumor-infiltrating effector cells expressing the immune checkpoint inhibitor PD-1 significantly decreased (p<0.05) in the treatment groups (PD-1, NK, NK+PD-1). The OS of mice that were treated with PD-1 antibody first followed by ex vivo activated NK cells was comparable to that of mice treated with the single regimens.

These promising preclinical results fit with the observations for the treatment of a patient with membrane Hsp70 positive, advanced NSCLC in stage IIIb, who was subjected to a combined therapy regimen consisting of RCT, NK cells and Nivolumab, a fully humanized antibody directed against PD-1; see Example 2.

DISCUSSION

A preclinical proof-of-principle study has been established and shown promising results of a combined therapy consisting of ex vivo Hsp70-stimulated NK cells and anti-PD-1 antibody with respect to local tumor control, OS and immune stimulation in mice with membrane Hsp70 positive glioblastomas. Antitumor responses in mice were accompanied by a massive infiltration of the glioblastomas with CD8⁺ cytotoxic lymphocytes and NK1.1 cells, and a reduction in the amount of PD-1⁺ immune cells in the tumor. Although NK cells or anti-PD-1 antibody, as a single treatment modality, have been shown to trigger antitumor immune responses that increase OS, a combined, sequential therapy has been found to be significantly more efficient.

Depending on its subcellular or extracellular localization, Hsp70 fulfils different functions [49]. On the one hand membrane Hsp70 serves as a tumor-specific target for Hsp70 peptide-activated NK cells [18, 20, 22, 47, 48], on the other hand, high cytosolic Hsp70 levels can interfere with apoptotic pathways that mediate therapy resistance. Therefore, Hsp70-specific NK cells or PD-1 antibody alone might not be sufficient for a complete tumor control.

Concomitant with the promising preclinical results of the combined therapy, a patient with advanced NSCLC was treated with a similar regimen consisting of RCT, NK cells and Nivolumab. Hsp70 positivity of the patient's tumor was confirmed by elevated exosomal Hsp70 (exHsp70) concentrations in the blood at diagnosis. Previously, exHsp70 has been shown to predict the membrane Hsp70 status of primary tumors and the viable tumor mass in tumor-bearing mice and human NSCLC patients [24]. In contrast, free Hsp70 in the blood circulation that predominantly originates from dying cells reflects responses to therapy. Therefore, free and exHsp70 were measured separately by two different ELISA systems [19]. The concentration of free Hsp70 that gradually increased between V0 and V7 might be a reflection of an enhanced tumor cell killing. In contrast, the drop in exHsp70 directly after RCT might be associated with a reduction in viable tumor mass. The transient increase after NK and Nivolumab therapy is most likely due to therapy-induced inflammation, since CRP values increased at the same time and inflammation also can cause the release of exHsp70.

Historically, RCT has been considered as being immunosuppressive because of large radiation fields that included substantial volumes of the blood and bone marrow [25]. Due to advances in radiation planning systems and equipment, it is nowadays possible to minimize damage on normal tissues. As a result, major parts of the bone marrow can be spared and immunosuppression can therefore be reduced. Moreover, RCT has been shown to induce immunogenic tumor cell death in preclinical models that in turn can elicit protective anti-tumor immune responses [26]. Because so far, it is not yet completely clear which dose, fractionation and therapy sequence is optimal for inducing anti-tumor immunity, these effects are rarely seen in clinical practice. In the presented Case Report, it was aimed to evaluate the composition of different immune cell subpopulations after sequential application of RCT, NK cell therapy and immune checkpoint inhibitor blockade in a patient with NSCLC (stage IIIB) who responded to therapy.

As previously shown for other tumor entities such as mammary and prostate carcinoma [27], RCT also had a negative impact on the B cell compartment in the patient with NSCLC. This finding is due to the high sensitivity of $CD19^+$ B cells towards radiotherapy [28]. However, already during, and even more pronounced after NK cell therapy, B cells recovered to initial levels and further increased thereafter. NK cells appear to play a key role in tumor immunosurveillance [29-32]. In addition to $CD8^+$ cytotoxic T cells [33], other studies have indicated that the overall survival of patients with oropharyngeal cancer positively correlates with high numbers of tumor-infiltrating $CD56^+$ NK cells [34]. Despite their inability to directly recognize antigen presented on MHC molecules, NK cells can selectively recognize target molecules via activatory receptors belonging either to the NKG2D or C-type lectin family [22, 35, 36]. Furthermore, B cells are important players in the cross-talk of the innate and adaptive immunity [37]. Therefore, a rapid recovery of the B cell compartment not only improves humoral immune responses, but also positively affects NK cell mediated cytotoxicity against tumor cells.

It is obvious that the success of an immune checkpoint inhibitor blockade requires the presence of antitumor reactive effector cells with the ability to infiltrate and recognize tumor cells [38, 39]. Therefore, the adoptive transfer of ex vivo activated NK cells that are triggered against the tumor-specific target membrane Hsp70 before the start of Nivolumab therapy might exert beneficial antitumor immune effects. The activity of NK cells not only depends on a complex network of inhibitory and activatory receptors with immune tyrosine-based inhibitory/activatory motives (ITIM/ITAM) [40], but also on the presence or absence of PD-1 receptors or other receptors such as for CTLA-4, PD-L1, Tim-3, CD96, KIR, NKG2A and TIGIT; see. e.g., Guillerey et al., Nature Immunol. 17 (2016), 1025-1036 for review. Therefore, the inhibition of the PD-1 pathway might be able to synergistically enhance the cytotoxicity of ex vivo stimulated NK cells against Hsp70 membrane positive tumor cells. However, depending on its subcellular or extracellular localization, Hsp70 can fulfil a variety of different functions [42]. Although membrane bound Hsp70 serves as a tumor-specific target for activated NK cells, high cytosolic Hsp70 levels interfere with apoptotic pathways that mediate therapy resistance.

Regulatory $CD4^+/CD25^+/FoxP3^+$ T (Treg) cells are well known to attenuate T as well as NK cell activity by the secretion of anti-inflammatory suppressive cytokines that impede cytotoxicity as well as migratory capacity of immunocompetent effector cells. Tumor patients have been shown to have higher levels of Treg cells in the periphery and in the tumor microenvironment [43]. Therefore, high Treg cell counts are associated with adverse clinical outcome. In our patient, RCT did not affect the percentage of $CD4^+$ Treg cells, however thereafter during NK cell therapy, a transient increase of this cell population was observed. This finding is most likely due to an RCT and NK cell therapy induced inflammation which results in a transient increase in IL-2 levels. However, during the follow-up period, the prevalence (percentage) of $CD4^+$ Treg cells continued to be below initial levels. The Nivolumab therapy further resulted in a decrease in Treg cells in the peripheral blood of our patient. As shown in preclinical models, a depletion of Treg cells could restore NK cell mediated anti-tumor immunity [44]. Therefore, it may be assumed that decreased numbers of Treg cells might further improve anti-tumor activity of the NK cells in our patient.

A recent study on lung cancer and Squamous Cell Carcinoma of the Head and Neck (SCCHN) demonstrated that an anti PD-1 therapy achieves higher response rates in tumors with high mutational loads which might reflected as greater levels of neoantigens. In line with this finding, our patient has a smoking history and thereby might have a higher mutational load. Although the PD-L1 expression on the tumor at diagnosis was low (1.1%), the patients might thereby have profited from the Nivolumab therapy.

In summary, blockade of immune checkpoint inhibitor such as the PD-1 pathway after Hsp70 based activation of NK cells seems to synergistically enhance and extend the cytolytic activity of stimulated NK cells against Hsp70 membrane positive tumor cells in a patient and thus leads to long-term control of the tumor.

REFERENCES

1. Ferlay J, Shin H R, Bray F, et al. Estimates of worldwide burden of cancer in 2008: GLOBOCAN 2008. Int J Cancer. 2010; 127:2893-917.
2. Travis W D. Pathology of lung cancer. Clin Chest Med. 2011; 32:669-92.
3. Oberije C, De Ruyssche D, Houben R, et al. A Validated Prediction Model for Overall Survival From Stage III Non-Small Cell Lung Cancer: Toward Survival Prediction for Individual Patients. Int J Radiat Oncol Biol Phys. 2015; 92:935-44.
4. Siva S, MacManus M P, Martin R F, et al. Abscopal effects of radiation therapy: a clinical review for the radiobiologist. Cancer Lett. 2015; 356:82-90.
5. Schmid T E, Multhoff G. Non-targeted effects of photon and particle irradiation and the interaction with the immune system. Front Oncol. 2012; 2:80.
6. Kang J, Demaria S, Formenti S. Current clinical trials testing the combination of immunotherapy with radiotherapy. J Immunother Cancer. 2016; 4:51.
7. Formenti S C, DeMaria S. Systemic effects of local radiotherapy. Lancet Oncol. 2009; 10:718-26.
8. Gandhi S, Chandna S. Radiation-induced inflammatory cascade and its reverberating crosstalks as potential cause of post-radiotherapy second malignancies. Cancer Metastasis Rev. 2017.
9. Vaupel P, Multhoff G. Adenosine can thwart antitumor immune responses elicited by radiotherapy: therapeutic strategies alleviating protumor ADO activitzies. Strahlenther Onkol. 2016; 192:279-87.192
10. Sharabi A B, Lim M, DeWeese T L, et al. Radiation and checkpoint blockade immunotherapy: radiosensitisation and potential mechanisms of synergy. Lancet Oncol. 2015; 16:e498-509.
11. Hanahan D, Weinberg R A. Hallmarks of cancer: the next generation. Cell. 2011; 144:646-74.
12. Mantovani A, Allavena P, Sica A, et al. Cancer-related inflammation. Nature. 2008; 454:436-44.
13. Schreiber R D, Old L J, Smyth M J. Cancer immunoediting: integrating immunity's roles in cancer suppression and promotion. Science. 2011; 331:1565-70.
14. Rizvi N A, Hellmann M D, Snyder A, et al. Cancer immunology. Mutational landscape determines sensitivity to PD-1 blockade in non-small cell lung cancer. Science. 2015; 348:124-8.
15. Pardoll D M. The blockade of immune checkpoints in cancer immunotherapy. Nat Rev Cancer. 2012; 12:252-64.
16. Brahmer J R, Drake C G, Wollner I, et al. Phase I study of single-agent anti-programmed death-1 (MDX-1106) in refractory solid tumors: safety, clinical activity, pharmacodynamics, and immunologic correlates. J Clin Oncol. 2010; 28:3167-75.
17. Rizvi N A, Mazieres J, Planchard D, et al. Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. 2015; 16:257-65.
18. Specht H M, Ahrens N, Blankenstein C, et al. Heat Shock Protein 70 (Hsp70) Peptide Activated Natural Killer (NK) Cells for the Treatment of Patients with Non-Small Cell Lung Cancer (NSCLC) after Radiochemotherapy (RCTx)—From Preclinical Studies to a Clinical Phase II Trial. Front Immunol. 2015; 6:162.
19. Breuninger S, Erl J, Knape C, et al. Quantitative analysis of liposomal heat shock protein 70 (Hsp70) in the blood of tumor patients using an novel LipHsp70 ELISA. Clinical Cellular Immunology. 2014; 5:2-10.
20. Stangl S, Gehrmann M, Riegger J, et al. Targeting membrane heat-shock protein 70 (Hsp70) on tumors by cmHsp70.1 antibody. ProcNatlAcadSciUSA. 2011; 108:733-8.
21. Eissner G, Kohlhuber F, Grell M, et al. Critical involvement of transmembrane tumor necrosis factor-alpha in endothelial programmed cell death mediated by ionizing radiation and bacterial endotoxin. Blood. 1995; 86:4184-93.
22. Gross C, Schmidt-Wolf I G, Nagaraj S, et al. Heat shock protein 70-reactivity is associated with increased cell surface density of CD94/CD56 on primary natural killer cells. Cell StressChaperones. 2003; 8:348-60.
23. Bayer C, Liebhardt M E, Schmid T E, et al. Validation of heat shock protein 70 as a tumor-specific biomarker for monitoring the outcome of radiation therapy in tumor mouse models. Int J Radiat Oncol Biol Phys. 2014; 88:694-700.
24. Gunther S, Ostheimer C, Stangl S, et al. Correlation of Hsp70 Serum Levels with Gross Tumor Volume and Composition of Lymphocyte Subpopulations in Patients with Squamous Cell and Adeno Non-Small Cell Lung Cancer. Front Immunol. 2015; 6:556.
25. Heidecke C D, Weighardt H, Feith M, et al. Neoadjuvant treatment of esophageal cancer: Immunosuppression following combined radiochemotherapy. Surgery. 2002; 132:495-501.
26. Demaria S, Golden E B, Formenti S C. Role of Local Radiation Therapy in Cancer Immunotherapy. JAMA Oncol. 2015.
27. Sage E K, Schmid T E, Sedelmayr M, et al. Comparative analysis of the effects of radiotherapy versus radiotherapy after adjuvant chemotherapy on the composition of lymphocyte subpopulations in breast cancer patients. Radiother Oncol. 2015.
28. Belka C, Ottinger H, Kreuzfelder E, et al. Impact of localized radiotherapy on blood immune cells counts and function in humans. Radiother Oncol. 1999; 50:199-204.
29 Vivier E, Raulet D H, Moretta A, et al. Innate or adaptive immunity? The example of natural killer cells. Science. 2011; 331:44-9.
30. Morvan M G, Lanier L L. NK cells and cancer: you can teach innate cells new tricks. Nat Rev Cancer. 2016; 16:7-19.
31. Raulet D H, Gasser S, Gowen B G, et al. Regulation of ligands for the NKG2D activating receptor. Annu Rev Immunol. 2013; 31:413-41.
32 Pross H F, Lotzova E. Role of natural killer cells in cancer. Nat Immun. 1993; 12:279-92.
33. Balermpas P, Rodel F, Krause M, et al. The PD-1/PD-L1 axis and human papilloma virus in patients with head and neck cancer after adjuvant chemoradiotherapy: A multicentre study of the German Cancer Consortium Radiation Oncology Group (DKTK-ROG). Int J Cancer. 2017; 141:594-603.
34. Wagner S, Wittekindt C, Reuschenbach M, et al. CD56-positive lymphocyte infiltration in relation to human papillomavirus association and prognostic significance in oropharyngeal squamous cell carcinoma. Int J Cancer. 2016; 138:2263-73.
35. Kruse P H, Matta J, Ugolini S, et al. Natural cytotoxicity receptors and their ligands. Immunol Cell Biol. 2014; 92:221-9.
36. Gross C, Hansch D, Gastpar R, et al. Interaction of heat shock protein 70 peptide with NK cells involves the NK receptor CD94. BiolChem. 2003; 384:267-79.
37 van Beek J J, Gorris M A, Skold A E, et al. Human blood myeloid and plasmacytoid dendritic cells cross activate each other and synergize in inducing NK cell cytotoxicity. Oncoimmunology. 2016; 5:e1227902.
38. Ariffin A B, Forde P F, Jahangeer S, et al. Releasing pressure in tumors: what do we know so far and where do we go from here? A review. Cancer Res. 2014; 74:2655-62.
39. Zitvogel L, Tesniere A, Kroemer G. Cancer despite immunosurveillance: immunoselection and immunosubversion. NatRevImmunol. 2006; 6:715-27.
40. Martinet L, Smyth M J. Balancing natural killer cell activation through paired receptors. Nat Rev Immunol. 2015; 15:243-54.
41. Benson D M, Jr., Bakan C E, Mishra A, et al. The PD-1/PD-L1 axis modulates the natural killer cell versus multiple myeloma effect: a therapeutic target for CT-011, a novel monoclonal anti-PD-1 antibody. Blood. 2010; 116:2286-94.
42. Jaattela M. Heat shock proteins as cellular lifeguards. AnnMed. 1999; 31:261-71.
43. Fecci P E, Mitchell D A, Whitesides J F, et al. Increased regulatory T-cell fraction amidst a diminished CD4 compartment explains cellular immune defects in patients with malignant glioma. Cancer Res. 2006; 66:3294-302.
44. Teng M W, Ngiow S F, von Scheidt B, et al. Conditional regulatory T-cell depletion releases adaptive immunity preventing carcinogenesis and suppressing established tumor growth. Cancer Res. 2010; 70:7800-9.
45. Mandal R, Senbabaoglu Y, Desrichard A, et al. The head and neck cancer immune landscape and its immunotherapeutic implications. JCI Insight. 2016; 1:e89829.
46. Stangl S, Foulds G A, Fellinger H, Pilkington G J, Pockley A G, Multhoff G. (2018) Immunohistochemical and flow cytometric analysis of intracellular and membrane-bound Hsp70, as a putative biomarker of glioblastoma multiforme, using the cmHsp70.1 monoclonal antibody. In: Calderwood S., Prince T. (eds) Chaperones. Methods in Molecular Biology, vol 1709. Humana Press, New York, NY, USA.
47. Multhoff G, Pfister K, Gehrmann M, et al. A 14-mer Hsp70 peptide stimulates natural killer (NK) cell activity. Cell Stress Chaperones. 2001; 6:337-44.
48. Krause S W, Gastpar R, Andreesen R, et al. Treatment of colon and lung cancer patients with ex vivo heat shock protein 70-peptide-activated, autologous natural killer cells: A clinical phase I trial. Clin Cancer Res. 2004; 10:3699-707.
49. Jäättelä M. Heat shock proteins as cellular lifeguards. Ann Med. 1999; 31:261-71.

The invention claimed is:

1. A method of treating or preventing relapse of a tumor in a subject in need thereof, comprising administering to the subject:
   (a) peripheral blood mononuclear cells (PBMCs) or a fraction thereof comprising natural killer (NK) cells, activated in vitro or ex vivo by a derivative of an Hsp70 protein, which is not complexed with peptides of tumor cells,
      wherein the Hsp70 protein derivative is a peptide of 30 or less amino acids,
      wherein the peptide comprises TKDNNLLGRFELSG (SEQ ID NO: 2), and
      wherein the peptide stimulates NK cell activity in combination with interleukin-2 (IL-2); and
   (b) a therapeutically effective amount of a monoclonal anti-PD1 antibody;
   wherein the tumor is a carcinoma and expresses cell surface Hsp70, and
   wherein the subject is suffering from or has been treated for non-small cell lung carcinoma (NSCLC).

2. The method according to claim 1, further comprising administering to the subject a conventional anti-tumor treatment which is radiochemotherapy with carboplatin or cisplatin.

3. The method according to claim 1, wherein the peptide consists of the amino acid sequence TKDNNLLGRFELSG (SEQ ID NO: 2).

4. The method according to claim 1, wherein the treatment includes an increase of the level of B lymphocytes and/or wherein the stimulated NK cell activity comprises proliferation of NK cells and/or cytolytic activity of NK cells.

5. The method according to claim 1, wherein the combination of the activated PMBCs or the fraction thereof and the monoclonal anti-PD1 antibody are administered together in a single composition or administered separately in two or more different compositions or dosage forms.

6. The method according to claim 1, wherein the method comprises the steps of:
   (a) administering to the subject a therapeutically effective amount of the activated PMBCs or the fraction thereof, and concurrently or subsequently
   (b) administering to the subject a therapeutically effective amount of the monoclonal anti-PD1 antibody.

7. The method according to claim 1, wherein the subject, compared to a corresponding healthy volunteer, shows a reduced level of CD3$^-$/CD19$^+$ B lymphocytes.

8. A method of treating or preventing relapse of a tumor, wherein the tumor is a carcinoma expressing cell surface Hsp70 in a subject who received a treatment comprising peripheral blood mononuclear cells (PBMCs) or a fraction thereof comprising natural killer (NK) cells, activated in vitro or ex vivo by a derivative of an Hsp70 protein, which is not complexed with peptides of tumor cells, wherein the Hsp70 protein derivative is a peptide of 30 or less amino acids, wherein the peptide comprises TKDNNLLGRFELSG (SEQ ID NO: 2), and wherein the peptide stimulates NK cell activity in combination with interleukin-2 (IL-2),
   the method comprising:
      administering to the subject a therapeutically effective amount of a monoclonal anti-PD1 antibody in combination with a conventional anti-tumor treatment, wherein the conventional anti-tumor treatment is radiochemotherapy with carboplatin or cisplatin, and wherein the subject is suffering from or has been treated for non-small cell lung carcinoma (NSCLC).

9. The method according to claim 1, wherein administration is performed via intravenous, intratumoral, subcutaneous or intraperitoneal route.

10. The method according to claim 1, further comprising, prior to administration of the activated PBMCs or the fraction thereof and the monoclonal anti-PD1 antibody, determining the presence and level of membrane Hsp70 expression on tumor cells in a sample from the subject.

11. The method according to claim 2, wherein the conventional anti-tumor treatment leads to depletion of $CD3^-$/$CD19^+$ B lymphocytes during and/or after the conventional anti-tumor treatment.

12. The method according to claim 1, wherein the monoclonal anti-PD1 antibody is Nivolumab.

13. The method according to claim 4, wherein the cytolytic activity against tumor cells is increased.

14. The method of claim 4, wherein the cytolytic activity against metastasizing cells of solid tumors is increased.

15. The method according to claim 6, wherein the subject prior to step (a) received a conventional anti-tumor treatment which is cisplatinum-based radiochemotherapy.

16. The method according to claim 15, wherein the conventional anti-tumor treatment led to the depletion of B lymphocytes.

17. The method according to claim 7, wherein the reduced level of $CD3^-$/$CD19^+$ B lymphocytes is due to a previous radiochemotherapy.

18. The method according to claim 10, wherein the presence and level of membrane Hsp70 expression on tumor cells in a sample from the subject is determined by using a cmHsp70.1 antibody.

* * * * *